United States Patent
Yang et al.

(10) Patent No.: US 11,485,784 B2
(45) Date of Patent: Nov. 1, 2022

(54) RANKING SYSTEM FOR IMMUNOGENIC CANCER-SPECIFIC EPITOPES

(71) Applicant: ACT Genomics (IP) Co., Ltd., Hong Kong (HK)

(72) Inventors: Pei-Jia Yang, Taipei (TW); Jen-Hao Cheng, Taipei (TW); Ying-Ja Chen, Taipei (TW); Shu-Jen Chen, Taipei (TW); Hua-Chien Chen, Taipei (TW)

(*) Notice: Subject to any disclaimer, the term of this patent is extended or adjusted under 35 U.S.C. 154(b) by 688 days.

(21) Appl. No.: 16/497,442

(22) PCT Filed: Mar. 31, 2018

(86) PCT No.: PCT/US2018/025597
§ 371 (c)(1),
(2) Date: Sep. 25, 2019

(87) PCT Pub. No.: WO2018/183980
PCT Pub. Date: Oct. 4, 2018

(65) Prior Publication Data
US 2021/0284738 A1    Sep. 16, 2021

Related U.S. Application Data

(60) Provisional application No. 62/479,320, filed on Mar. 31, 2017.

(51) Int. Cl.
*G16B 20/00* (2019.01)
*C07K 16/28* (2006.01)
(Continued)

(52) U.S. Cl.
CPC .... *C07K 16/2833* (2013.01); *C07K 14/70539* (2013.01); *G16B 20/00* (2019.02); *A61K 38/00* (2013.01); *C07K 2317/92* (2013.01)

(58) Field of Classification Search
CPC .......... C07K 16/2833; C07K 14/70539; C07K 2317/92; G16B 20/00; G16B 40/20; A61K 38/00; A61K 39/0011
(Continued)

(56) References Cited

U.S. PATENT DOCUMENTS

| | | |
|---|---|---|
| 2015/0352201 A1 | 12/2015 | David et al. |
| 2016/0069895 A1* | 3/2016 | Delamarre .............. A61P 43/00 |
| | | 435/6.12 |
| 2016/0101170 A1 | 4/2016 | Hacohen et al. |

FOREIGN PATENT DOCUMENTS

| | | |
|---|---|---|
| CN | 107704727 A | 2/2018 |
| WO | WO2013040142 A2 | 3/2013 |

(Continued)

OTHER PUBLICATIONS

Office Action from the Taiwan Intellectual Property Office, dated May 22, 2019.
Office Action from the JPO, dated Nov. 17, 2020.
Extended European search report from the EPO, dated Dec. 21, 2020.
(Continued)

*Primary Examiner* — Michael Maskell
(74) *Attorney, Agent, or Firm* — OPES IP Consulting Co. Ltd.

(57) ABSTRACT

This disclosure relates to systems and methods that identify, predict, and rank immunogenic T-cell epitopes. In particular, this disclosure identifies epitopes that arose from disease-associated mutations, wherein the epitopes are predicted to elicit immune response from T cells. Specifically, this disclosure simultaneously considers peptide-level information, including MHC Class I and II presentation, helper and cytotoxic T cell response and sample-level information, including mutation clonality and MHC allele dosage. In some embodiment, the systems and methods are used for personalized treatment of cancers.

20 Claims, 7 Drawing Sheets
Specification includes a Sequence Listing.

(51) Int. Cl.
 *C07K 14/74* (2006.01)
 *A61K 38/00* (2006.01)

(58) Field of Classification Search
 USPC .................................... 702/19, 20; 436/173
 See application file for complete search history.

(56) References Cited

FOREIGN PATENT DOCUMENTS

| | | |
|---|---|---|
| WO | WO 2016128060 A1 | 8/2016 |
| WO | WO2016174085 A1 | 11/2016 |
| WO | WO2017011660 A1 | 1/2017 |

OTHER PUBLICATIONS

Office Action from the JPO, dated Nov. 9, 2021.
Capasso et al. "A Novel In Silico Framework to Imporve MHC-I Epitopes and Break the Tolerance to Melanoma," OncoImmunology, May 11, 2017 (May 11, 2017), vol. 6, Iss. 9, pp. 1-14, entire document.
De Groot et al., "Prediction of Immunogenicity for Therapeutic Proteins: State of the Art," Currenct Opinion in Drug Discovery & Development, May 1, 2007 (May 1, 2007), vol. 10, Iss. 3, pp. 1-9. entire document.
Reche et al., "Enhancement to the RANKPEP resource for the prediction of peptide binding to MHC molecules using profiles," Immunogenetics, Sep. 3, 2004 (Sep. 3, 2004), vol. 569, Iss. 6, pp. 405-419. entire document.

\* cited by examiner

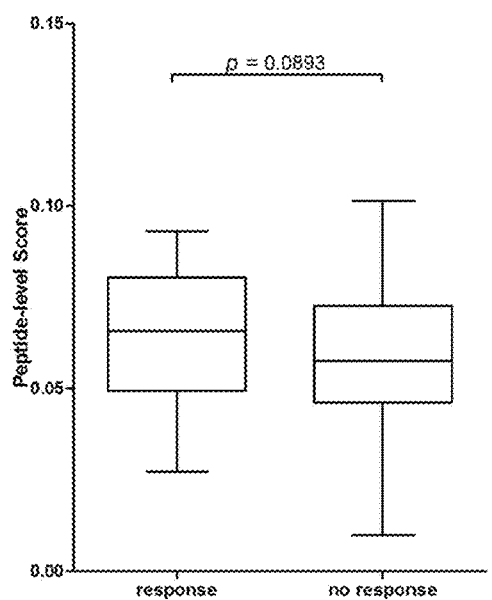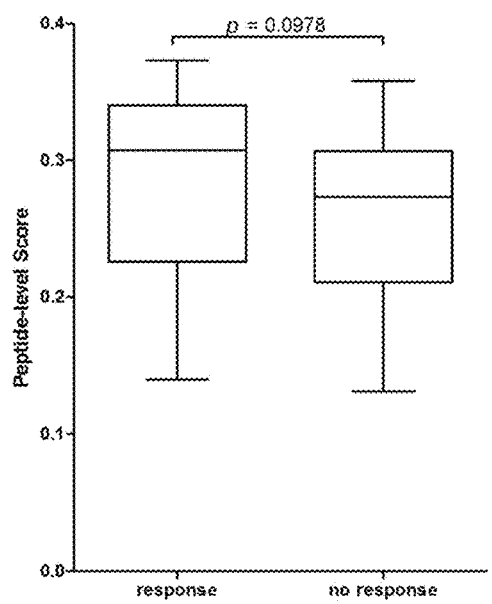
FIGURE 6A
FIGURE 6B
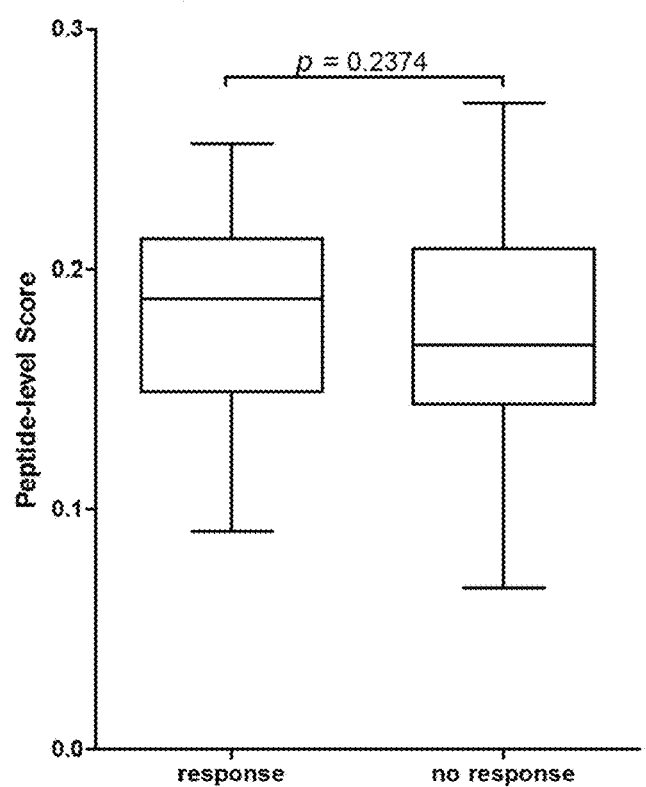
FIGURE 6C

SEQUENCE LISTING

<160> NUMBER OF SEQ ID NOS: 100

<210> SEQ ID NO 1
<211> LENGTH: 9
<212> TYPE: PRT
<213> ORGANISM: Artificial Sequence
<220> FEATURE:
<223> OTHER INFORMATION: IMPID: 1-IMP04

<400> SEQUENCE: 1

Lys Leu Lys Phe Val Thr Leu Val Phe
1               5

<210> SEQ ID NO 2
<211> LENGTH: 10
<212> TYPE: PRT
<213> ORGANISM: Artificial Sequence
<220> FEATURE:
<223> OTHER INFORMATION: IMPID: 1-IMP07

<400> SEQUENCE: 2

Arg Phe Leu Glu Tyr Leu Pro Leu Arg Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: IMPID: 1-IMP02

<400> SEQUENCE: 3

Val Gln Lys Val Ala Ser Lys Ile Pro Phe
1               5                   10

```
<210> SEQ ID NO 4
<211> LENGTH: 9
<212> TYPE: PRT
<213> ORGANISM: Artificial Sequence
<220> FEATURE:
<223> OTHER INFORMATION: IMPID: 1-IMP06

<400> SEQUENCE: 4

Thr Leu Phe His Thr Phe Tyr Glu Leu
1               5

<210> SEQ ID NO 5
<211> LENGTH: 10
<212> TYPE: PRT
<213> ORGANISM: Artificial Sequence
<220> FEATURE:
<223> OTHER INFORMATION: IMPID: 1-IMP06

<400> SEQUENCE: 5

Thr Leu Phe His Thr Phe Tyr Glu Leu Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: IMPID: 1-IMP11

<400> SEQUENCE: 6

Lys Phe Gly Asp Leu Thr Asn Asn Phe
1               5

<210> SEQ ID NO 7
<211> LENGTH: 9
<212> TYPE: PRT
<213> ORGANISM: Artificial Sequence
<220> FEATURE:
<223> OTHER INFORMATION: IMPID: 1-IMP26

<400> SEQUENCE: 7

Pro Arg Glu Glu Phe Leu Arg Leu Cys
1               5

<210> SEQ ID NO 8
<211> LENGTH: 9
<212> TYPE: PRT
<213> ORGANISM: Artificial Sequence
<220> FEATURE:
<223> OTHER INFORMATION: IMPID: 1-IMP08

<400> SEQUENCE: 8

Lys Leu Phe Glu Ser Lys Ala Glu Leu
1               5

<210> SEQ ID NO 9
<211> LENGTH: 9
<212> TYPE: PRT
<213> ORGANISM: Artificial Sequence
<220> FEATURE:
<223> OTHER INFORMATION: IMPID: 1-IMP17

<400> SEQUENCE: 9

Leu Cys Pro Arg Glu Glu Phe Leu Arg
1               5

<210> SEQ ID NO 10
```

```
<211> LENGTH: 10
<212> TYPE: PRT
<213> ORGANISM: Artificial Sequence
<220> FEATURE:
<223> OTHER INFORMATION: IMPID: 1-IMP02

<400> SEQUENCE: 10

Pro Phe Pro Asp Arg Ile Thr Glu Glu Ser
1               5                   10

<210> SEQ ID NO 11
<211> LENGTH: 9
<212> TYPE: PRT
<213> ORGANISM: Artificial Sequence
<220> FEATURE:
<223> OTHER INFORMATION: IMPID: 1-IMP04

<400> SEQUENCE: 11

Val Leu Ala Lys Lys Leu Lys Phe Val
1               5

<210> SEQ ID NO 12
<211> LENGTH: 9
<212> TYPE: PRT
<213> ORGANISM: Artificial Sequence
<220> FEATURE:
<223> OTHER INFORMATION: IMPID: 1-IMP03

<400> SEQUENCE: 12

Lys Lys Lys Trp Phe Leu Phe Gln Asp
1               5

<210> SEQ ID NO 13
<211> LENGTH: 9
<212> TYPE: PRT
<213> ORGANISM: Artificial Sequence
<220> FEATURE:
<223> OTHER INFORMATION: IMPID: 1-IMP02

<400> SEQUENCE: 13

Pro Phe Pro Asp Arg Ile Thr Glu Glu
1               5

<210> SEQ ID NO 14
<211> LENGTH: 9
<212> TYPE: PRT
<213> ORGANISM: Artificial Sequence
<220> FEATURE:
<223> OTHER INFORMATION: IMPID: 1-IMP07

<400> SEQUENCE: 14

His Thr Glu Leu Glu Arg Phe Leu Glu
1               5

<210> SEQ ID NO 15
<211> LENGTH: 10
<212> TYPE: PRT
<213> ORGANISM: Artificial Sequence
<220> FEATURE:
<223> OTHER INFORMATION: IMPID: 1-IMP08

<400> SEQUENCE: 15

Lys Leu Phe Glu Ser Lys Ala Glu Leu Ala
1               5                   10

<210> SEQ ID NO 16
<211> LENGTH: 9
```

```
<212> TYPE: PRT
<213> ORGANISM: Artificial Sequence
<220> FEATURE:
<223> OTHER INFORMATION: IMPID: 1-IMP07

<400> SEQUENCE: 16

Thr Glu Leu Glu Arg Phe Leu Glu Tyr
1               5

<210> SEQ ID NO 17
<211> LENGTH: 9
<212> TYPE: PRT
<213> ORGANISM: Artificial Sequence
<220> FEATURE:
<223> OTHER INFORMATION: IMPID: 1-IMP07

<400> SEQUENCE: 17

Leu Leu His Thr Glu Leu Glu Arg Phe
1               5

<210> SEQ ID NO 18
<211> LENGTH: 9
<212> TYPE: PRT
<213> ORGANISM: Artificial Sequence
<220> FEATURE:
<223> OTHER INFORMATION: IMPID: 1-IMP02

<400> SEQUENCE: 18

Phe Pro Asp Arg Ile Thr Glu Glu Ser
1               5

<210> SEQ ID NO 19
<211> LENGTH: 10
<212> TYPE: PRT
<213> ORGANISM: Artificial Sequence
<220> FEATURE:
<223> OTHER INFORMATION: IMPID: 1-IMP19

<400> SEQUENCE: 19

Val Ser Val Gly Asp Phe Ser Gln Glu Phe
1               5                   10

<210> SEQ ID NO 20
<211> LENGTH: 10
<212> TYPE: PRT
<213> ORGANISM: Artificial Sequence
<220> FEATURE:
<223> OTHER INFORMATION: IMPID: 1-IMP02

<400> SEQUENCE: 20

Ile Pro Phe Pro Asp Arg Ile Thr Glu Glu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: IMPID: 1-IMP17

<400> SEQUENCE: 21

Cys Pro Arg Glu Glu Phe Leu Arg Leu Cys
1               5                   10

<210> SEQ ID NO 22
<211> LENGTH: 9
<212> TYPE: PRT
```

```
<213> ORGANISM: Artificial Sequence
<220> FEATURE:
<223> OTHER INFORMATION: IMPID: 1-IMP12

<400> SEQUENCE: 22

Ala Leu Phe Ala Ser Arg Pro Arg Phe
1               5

<210> SEQ ID NO 23
<211> LENGTH: 9
<212> TYPE: PRT
<213> ORGANISM: Artificial Sequence
<220> FEATURE:
<223> OTHER INFORMATION: IMPID: 1-IMP03

<400> SEQUENCE: 23

Phe Leu Phe Gln Asp Ser Lys Lys Ile
1               5

<210> SEQ ID NO 24
<211> LENGTH: 9
<212> TYPE: PRT
<213> ORGANISM: Artificial Sequence
<220> FEATURE:
<223> OTHER INFORMATION: IMPID: 1-IMP08

<400> SEQUENCE: 24

Asp Lys Leu Phe Glu Ser Lys Ala Glu
1               5

<210> SEQ ID NO 25
<211> LENGTH: 10
<212> TYPE: PRT
<213> ORGANISM: Artificial Sequence
<220> FEATURE:
<223> OTHER INFORMATION: IMPID: 1-IMP03

<400> SEQUENCE: 25

Ser Lys Lys Lys Trp Phe Leu Phe Gln Asp
1               5                   10

<210> SEQ ID NO 26
<211> LENGTH: 9
<212> TYPE: PRT
<213> ORGANISM: Artificial Sequence
<220> FEATURE:
<223> OTHER INFORMATION: IMPID: 1-IMP02

<400> SEQUENCE: 26

Ile Pro Phe Pro Asp Arg Ile Thr Glu
1               5

<210> SEQ ID NO 27
<211> LENGTH: 9
<212> TYPE: PRT
<213> ORGANISM: Artificial Sequence
<220> FEATURE:
<223> OTHER INFORMATION: IMPID: 1-IMP12

<400> SEQUENCE: 27

Gly Gly Ala Leu Phe Ala Ser Arg Pro
1               5

<210> SEQ ID NO 28
<211> LENGTH: 10
<212> TYPE: PRT
<213> ORGANISM: Artificial Sequence
```

```
<220> FEATURE:
<223> OTHER INFORMATION: IMPID: 1-IMP07

<400> SEQUENCE: 28

Leu His Thr Glu Leu Glu Arg Phe Leu Glu
1               5                   10

<210> SEQ ID NO 29
<211> LENGTH: 9
<212> TYPE: PRT
<213> ORGANISM: Artificial Sequence
<220> FEATURE:
<223> OTHER INFORMATION: IMPID: 1-IMP26

<400> SEQUENCE: 29

Leu Ser Pro Arg Glu Glu Phe Leu Arg
1               5

<210> SEQ ID NO 30
<211> LENGTH: 10
<212> TYPE: PRT
<213> ORGANISM: Artificial Sequence
<220> FEATURE:
<223> OTHER INFORMATION: IMPID: 1-IMP26

<400> SEQUENCE: 30

Ser Pro Arg Glu Glu Phe Leu Arg Leu Cys
1               5                   10

<210> SEQ ID NO 31
<211> LENGTH: 9
<212> TYPE: PRT
<213> ORGANISM: Artificial Sequence
<220> FEATURE:
<223> OTHER INFORMATION: IMPID: 1-IMP19

<400> SEQUENCE: 31

Val Gly Asp Phe Ser Gln Glu Phe Ser
1               5

<210> SEQ ID NO 32
<211> LENGTH: 10
<212> TYPE: PRT
<213> ORGANISM: Artificial Sequence
<220> FEATURE:
<223> OTHER INFORMATION: IMPID: 1-IMP03

<400> SEQUENCE: 32

Lys Lys Lys Trp Phe Leu Phe Gln Asp Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: IMPID: 1-IMP10

<400> SEQUENCE: 33

Asp Ser Gly Ile Pro Glu Asn Ser Phe Asn
1               5                   10

<210> SEQ ID NO 34
<211> LENGTH: 10
<212> TYPE: PRT
<213> ORGANISM: Artificial Sequence
<220> FEATURE:
```

```
<223> OTHER INFORMATION: IMPID: 1-IMP19

<400> SEQUENCE: 34

Val Gly Asp Phe Ser Gln Glu Phe Ser Pro
1               5                   10

<210> SEQ ID NO 35
<211> LENGTH: 10
<212> TYPE: PRT
<213> ORGANISM: Artificial Sequence
<220> FEATURE:
<223> OTHER INFORMATION: IMPID: 1-IMP12

<400> SEQUENCE: 35

Arg Gly Gly Ala Leu Phe Ala Ser Arg Pro
1               5                   10

<210> SEQ ID NO 36
<211> LENGTH: 9
<212> TYPE: PRT
<213> ORGANISM: Artificial Sequence
<220> FEATURE:
<223> OTHER INFORMATION: IMPID: 1-IMP19

<400> SEQUENCE: 36

Ser Val Gly Asp Phe Ser Gln Glu Phe
1               5

<210> SEQ ID NO 37
<211> LENGTH: 9
<212> TYPE: PRT
<213> ORGANISM: Artificial Sequence
<220> FEATURE:
<223> OTHER INFORMATION: IMPID: 1-IMP10

<400> SEQUENCE: 37

Leu Ala Asp Ser Gly Ile Pro Glu Asn
1               5

<210> SEQ ID NO 38
<211> LENGTH: 9
<212> TYPE: PRT
<213> ORGANISM: Artificial Sequence
<220> FEATURE:
<223> OTHER INFORMATION: IMPID: 1-IMP04

<400> SEQUENCE: 38

Lys Lys Leu Lys Phe Val Thr Leu Val
1               5

<210> SEQ ID NO 39
<211> LENGTH: 10
<212> TYPE: PRT
<213> ORGANISM: Artificial Sequence
<220> FEATURE:
<223> OTHER INFORMATION: IMPID: 1-IMP04

<400> SEQUENCE: 39

Ser Lys Ile Pro Phe Pro Asp Arg Ile Thr
1               5                   10

<210> SEQ ID NO 40
<211> LENGTH: 9
<212> TYPE: PRT
<213> ORGANISM: Artificial Sequence
<220> FEATURE:
<223> OTHER INFORMATION: IMPID: 1-IMP10
```

```
<400> SEQUENCE: 40

Gly Ile Pro Glu Asn Ser Phe Asn Val
1               5

<210> SEQ ID NO 41
<211> LENGTH: 9
<212> TYPE: PRT
<213> ORGANISM: Artificial Sequence
<220> FEATURE:
<223> OTHER INFORMATION: IMPID: 1-IMP02

<400> SEQUENCE: 41

Lys Ile Pro Phe Pro Asp Arg Ile Thr
1               5

<210> SEQ ID NO 42
<211> LENGTH: 9
<212> TYPE: PRT
<213> ORGANISM: Artificial Sequence
<220> FEATURE:
<223> OTHER INFORMATION: IMPID: 1-IMP11

<400> SEQUENCE: 42

Gly Lys Phe Gly Asp Leu Thr Asn Asn
1               5

<210> SEQ ID NO 43
<211> LENGTH: 9
<212> TYPE: PRT
<213> ORGANISM: Artificial Sequence
<220> FEATURE:
<223> OTHER INFORMATION: IMPID: 1-IMP08

<400> SEQUENCE: 43

Asp Ser Asp Lys Leu Phe Glu Ser Lys
1               5

<210> SEQ ID NO 44
<211> LENGTH: 9
<212> TYPE: PRT
<213> ORGANISM: Artificial Sequence
<220> FEATURE:
<223> OTHER INFORMATION: IMPID: 1-IMP08

<400> SEQUENCE: 44

Glu Asp Ser Asp Lys Leu Phe Glu Ser
1               5

<210> SEQ ID NO 45
<211> LENGTH: 10
<212> TYPE: PRT
<213> ORGANISM: Artificial Sequence
<220> FEATURE:
<223> OTHER INFORMATION: IMPID: 1-IMP07

<400> SEQUENCE: 45

Leu Leu His Thr Glu Leu Glu Arg Phe Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: IMPID: 1-IMP12
```

<400> SEQUENCE: 46

Arg Arg Gly Gly Ala Leu Phe Ala Ser Arg
1               5                   10

<210> SEQ ID NO 47
<211> LENGTH: 9
<212> TYPE: PRT
<213> ORGANISM: Artificial Sequence
<220> FEATURE:
<223> OTHER INFORMATION: IMPID: 1-IMP10

<400> SEQUENCE: 47

Ile Pro Glu Asn Ser Phe Asn Val Ser
1               5

<210> SEQ ID NO 48
<211> LENGTH: 9
<212> TYPE: PRT
<213> ORGANISM: Artificial Sequence
<220> FEATURE:
<223> OTHER INFORMATION: IMPID: 1-IMP02

<400> SEQUENCE: 48

Ala Ser Lys Ile Pro Phe Pro Asp Arg
1               5

<210> SEQ ID NO 49
<211> LENGTH: 10
<212> TYPE: PRT
<213> ORGANISM: Artificial Sequence
<220> FEATURE:
<223> OTHER INFORMATION: IMPID: 1-IMP06

<400> SEQUENCE: 49

Leu Phe His Thr Phe Tyr Glu Leu Leu Ile
1               5                   10

<210> SEQ ID NO 50
<211> LENGTH: 10
<212> TYPE: PRT
<213> ORGANISM: Artificial Sequence
<220> FEATURE:
<223> OTHER INFORMATION: IMPID: 1-IMP07

<400> SEQUENCE: 50

Ile Leu Leu His Thr Glu Leu Glu Arg Phe
1               5                   10

<210> SEQ ID NO 51
<211> LENGTH: 21
<212> TYPE: PRT
<213> ORGANISM: Artificial Sequence
<220> FEATURE:
<223> OTHER INFORMATION: VarID: chr16_67440152_C>T

<400> SEQUENCE: 51

Leu Tyr Leu Phe Phe Ala Val Ile Gly Phe Glu Ile Leu Val Pro Leu
1               5                   10                  15

Leu Pro His His Trp
            20

<210> SEQ ID NO 52
<211> LENGTH: 17
<212> TYPE: PRT
<213> ORGANISM: Artificial Sequence
<220> FEATURE:

```
<223> OTHER INFORMATION: VarID: chr16_67440152_C>T

<400> SEQUENCE: 52

Leu Tyr Leu Phe Phe Ala Val Ile Gly Phe Glu Ile Leu Val Pro Leu
1               5                   10                  15

Leu

<210> SEQ ID NO 53
<211> LENGTH: 23
<212> TYPE: PRT
<213> ORGANISM: Artificial Sequence
<220> FEATURE:
<223> OTHER INFORMATION: VarID: chr16_67440152_C>T

<400> SEQUENCE: 53

His Pro Leu Gln Ile Val Ala Trp Leu Leu Tyr Leu Phe Phe Ala Val
1               5                   10                  15

Ile Gly Phe Glu Ile Leu Val
            20

<210> SEQ ID NO 54
<211> LENGTH: 21
<212> TYPE: PRT
<213> ORGANISM: Artificial Sequence
<220> FEATURE:
<223> OTHER INFORMATION: VarID: chr17_28511815_G>T

<400> SEQUENCE: 54

Arg Val Asn Phe Arg Arg Glu Lys Val Ile Glu Thr Pro Glu Asn Asp
1               5                   10                  15

Phe Lys His His Arg
            20

<210> SEQ ID NO 55
<211> LENGTH: 12
<212> TYPE: PRT
<213> ORGANISM: Artificial Sequence
<220> FEATURE:
<223> OTHER INFORMATION: VarID: chr16_67440152_C>T

<400> SEQUENCE: 55

Leu Tyr Leu Phe Phe Ala Val Ile Gly Phe Glu Ile
1               5                   10

<210> SEQ ID NO 56
<211> LENGTH: 9
<212> TYPE: PRT
<213> ORGANISM: Artificial Sequence
<220> FEATURE:
<223> OTHER INFORMATION: VarID: chr10_18122699_G>A

<400> SEQUENCE: 56

Ser Thr Leu Thr Trp His Gln Ala Arg
1               5

<210> SEQ ID NO 57
<211> LENGTH: 13
<212> TYPE: PRT
<213> ORGANISM: Artificial Sequence
<220> FEATURE:
<223> OTHER INFORMATION: VarID: chr16_67440152_C>T

<400> SEQUENCE: 57

Leu Tyr Leu Phe Phe Ala Val Ile Gly Phe Glu Ile Leu
1               5                   10
```

<210> SEQ ID NO 58
<211> LENGTH: 22
<212> TYPE: PRT
<213> ORGANISM: Artificial Sequence
<220> FEATURE:
<223> OTHER INFORMATION: VarID: chr16_67440152_C>T

<400> SEQUENCE: 58

Leu Tyr Leu Phe Phe Ala Val Ile Gly Phe Glu Ile Leu Val Pro Leu
1               5                   10                  15

Leu Pro His His Trp Val
            20

<210> SEQ ID NO 59
<211> LENGTH: 12
<212> TYPE: PRT
<213> ORGANISM: Artificial Sequence
<220> FEATURE:
<223> OTHER INFORMATION: VarID: chr2_165984466_C>T

<400> SEQUENCE: 59

Lys Met Gln Glu Cys Phe Gln Lys Ala Phe Phe Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: VarID: chr16_67440152_C>T

<400> SEQUENCE: 60

Leu Tyr Leu Phe Phe Ala Val Ile Gly Phe Glu Ile Leu Val
1               5                   10

<210> SEQ ID NO 61
<211> LENGTH: 18
<212> TYPE: PRT
<213> ORGANISM: Artificial Sequence
<220> FEATURE:
<223> OTHER INFORMATION: VarID: chr17_28511815_G>T

<400> SEQUENCE: 61

Arg Val Asn Phe Arg Arg Glu Lys Val Ile Glu Thr Pro Glu Asn Asp
1               5                   10                  15

Phe Lys

<210> SEQ ID NO 62
<211> LENGTH: 20
<212> TYPE: PRT
<213> ORGANISM: Artificial Sequence
<220> FEATURE:
<223> OTHER INFORMATION: VarID: chr16_67440152_C>T

<400> SEQUENCE: 62

Ala Trp Leu Leu Tyr Leu Phe Phe Ala Val Ile Gly Phe Glu Ile Leu
1               5                   10                  15

Val Pro Leu Leu
            20

<210> SEQ ID NO 63
<211> LENGTH: 18
<212> TYPE: PRT
<213> ORGANISM: Artificial Sequence

```
<220> FEATURE:
<223> OTHER INFORMATION: VarID: chr16_67440152_C>T

<400> SEQUENCE: 63

Phe Phe Ala Val Ile Gly Phe Glu Ile Leu Val Pro Leu Leu Pro His
1               5                   10                  15

His Trp

<210> SEQ ID NO 64
<211> LENGTH: 8
<212> TYPE: PRT
<213> ORGANISM: Artificial Sequence
<220> FEATURE:
<223> OTHER INFORMATION: VarID: chr17_28511815_G>T

<400> SEQUENCE: 64

Arg Val Asn Phe Arg Arg Glu Lys
1               5

<210> SEQ ID NO 65
<211> LENGTH: 21
<212> TYPE: PRT
<213> ORGANISM: Artificial Sequence
<220> FEATURE:
<223> OTHER INFORMATION: VarID: chr17_72832365_C>T

<400> SEQUENCE: 65

Met Tyr Thr Leu Asn Phe Ala Cys Cys Asp Val Val Gly Leu Ala Ala
1               5                   10                  15

Val Arg Phe Phe Leu
            20

<210> SEQ ID NO 66
<211> LENGTH: 8
<212> TYPE: PRT
<213> ORGANISM: Artificial Sequence
<220> FEATURE:
<223> OTHER INFORMATION: VarID: chr10_18122699_G>A

<400> SEQUENCE: 66

Thr Leu Thr Trp His Gln Ala Arg
1               5

<210> SEQ ID NO 67
<211> LENGTH: 18
<212> TYPE: PRT
<213> ORGANISM: Artificial Sequence
<220> FEATURE:
<223> OTHER INFORMATION: VarID: chr8_41552157_T>C

<400> SEQUENCE: 67

Lys Leu Val Pro Leu Val Gln Ala Ala Phe Pro Glu Asn Ala Val Thr
1               5                   10                  15

Lys Arg

<210> SEQ ID NO 68
<211> LENGTH: 10
<212> TYPE: PRT
<213> ORGANISM: Artificial Sequence
<220> FEATURE:
<223> OTHER INFORMATION: VarID: chr10_18122699_G>A

<400> SEQUENCE: 68

Lys Ser Thr Leu Thr Trp His Gln Ala Arg
1               5                   10
```

```
<210> SEQ ID NO 69
<211> LENGTH: 15
<212> TYPE: PRT
<213> ORGANISM: Artificial Sequence
<220> FEATURE:
<223> OTHER INFORMATION: VarID: chr16_67440152_C>T

<400> SEQUENCE: 69

Ala Trp Leu Leu Tyr Leu Phe Phe Ala Val Ile Gly Phe Glu Ile
1               5                   10                  15

<210> SEQ ID NO 70
<211> LENGTH: 20
<212> TYPE: PRT
<213> ORGANISM: Artificial Sequence
<220> FEATURE:
<223> OTHER INFORMATION: VarID: chr8_41552157_T>C

<400> SEQUENCE: 70

Lys Ser Lys Leu Val Pro Leu Val Gln Ala Ala Phe Pro Glu Asn Ala
1               5                   10                  15

Val Thr Lys Arg
            20

<210> SEQ ID NO 71
<211> LENGTH: 21
<212> TYPE: PRT
<213> ORGANISM: Artificial Sequence
<220> FEATURE:
<223> OTHER INFORMATION: VarID: chr1_209849154_T>G

<400> SEQUENCE: 71

Ala Leu Phe Gly Val Val Leu Gly Arg Met Glu Thr Val Cys Ser Pro
1               5                   10                  15

Phe Thr Ala Ala Arg
            20

<210> SEQ ID NO 72
<211> LENGTH: 17
<212> TYPE: PRT
<213> ORGANISM: Artificial Sequence
<220> FEATURE:
<223> OTHER INFORMATION: VarID: chr1_209849154_T>G

<400> SEQUENCE: 72

Val Val Leu Gly Arg Met Glu Thr Val Cys Ser Pro Phe Thr Ala Ala
1               5                   10                  15

Arg

<210> SEQ ID NO 73
<211> LENGTH: 18
<212> TYPE: PRT
<213> ORGANISM: Artificial Sequence
<220> FEATURE:
<223> OTHER INFORMATION: VarID: chr1_209849154_T>G

<400> SEQUENCE: 73

Lys Leu Tyr Val Leu Gly Ser Val Leu Ala Leu Phe Gly Val Val Leu
1               5                   10                  15

Gly Arg

<210> SEQ ID NO 74
<211> LENGTH: 10
```

```
<212> TYPE: PRT
<213> ORGANISM: Artificial Sequence
<220> FEATURE:
<223> OTHER INFORMATION: VarID: chr10_18122699_G>A

<400> SEQUENCE: 74

Ser Thr Leu Thr Trp His Gln Ala Arg Lys
1               5                   10

<210> SEQ ID NO 75
<211> LENGTH: 20
<212> TYPE: PRT
<213> ORGANISM: Artificial Sequence
<220> FEATURE:
<223> OTHER INFORMATION: VarID: chr1_209849154_T>G

<400> SEQUENCE: 75

Val Val Leu Gly Arg Met Glu Thr Val Cys Ser Pro Phe Thr Ala Ala
1               5                   10                  15

Arg Arg Leu Arg
            20

<210> SEQ ID NO 76
<211> LENGTH: 9
<212> TYPE: PRT
<213> ORGANISM: Artificial Sequence
<220> FEATURE:
<223> OTHER INFORMATION: VarID: chr10_24896718_G>T

<400> SEQUENCE: 76

Lys Thr Ser Ala Pro Leu Ile Arg Arg
1               5

<210> SEQ ID NO 77
<211> LENGTH: 20
<212> TYPE: PRT
<213> ORGANISM: Artificial Sequence
<220> FEATURE:
<223> OTHER INFORMATION: VarID: chr17_72832365_C>T

<400> SEQUENCE: 77

Met Tyr Thr Leu Asn Phe Ala Cys Cys Asp Val Val Gly Leu Ala Ala
1               5                   10                  15

Val Arg Phe Phe
            20

<210> SEQ ID NO 78
<211> LENGTH: 13
<212> TYPE: PRT
<213> ORGANISM: Artificial Sequence
<220> FEATURE:
<223> OTHER INFORMATION: VarID: chr8_41552157_T>C

<400> SEQUENCE: 78

Val Pro Leu Val Gln Ala Ala Phe Pro Glu Asn Ala Val
1               5                   10

<210> SEQ ID NO 79
<211> LENGTH: 13
<212> TYPE: PRT
<213> ORGANISM: Artificial Sequence
<220> FEATURE:
<223> OTHER INFORMATION: VarID: chr2_165984466_C>T

<400> SEQUENCE: 79

Lys Met Gln Glu Cys Phe Gln Lys Ala Phe Phe Arg Lys
```

<210> SEQ ID NO 80
<211> LENGTH: 19
<212> TYPE: PRT
<213> ORGANISM: Artificial Sequence
<220> FEATURE:
<223> OTHER INFORMATION: VarID: chr17_72832365_C>T

<400> SEQUENCE: 80

Met Tyr Thr Leu Asn Phe Ala Cys Cys Asp Val Val Gly Leu Ala Ala
1               5                   10                  15
Val Arg Phe

<210> SEQ ID NO 81
<211> LENGTH: 9
<212> TYPE: PRT
<213> ORGANISM: Artificial Sequence
<220> FEATURE:
<223> OTHER INFORMATION: VarID: chr1_209849154_T>G

<400> SEQUENCE: 81

Ala Leu Phe Gly Val Val Leu Gly Arg
1               5

<210> SEQ ID NO 82
<211> LENGTH: 10
<212> TYPE: PRT
<213> ORGANISM: Artificial Sequence
<220> FEATURE:
<223> OTHER INFORMATION: VarID: chr2_74328527_G>A

<400> SEQUENCE: 82

Ser Leu Thr Glu Lys Pro Trp Ala Leu Arg
1               5                   10

<210> SEQ ID NO 83
<211> LENGTH: 16
<212> TYPE: PRT
<213> ORGANISM: Artificial Sequence
<220> FEATURE:
<223> OTHER INFORMATION: VarID: chr17_28511815_G>T

<400> SEQUENCE: 83

Lys Ser Ser Ala Asp Asp Glu Ile Glu Glu Thr Arg Val Asn Phe Arg
1               5                   10                  15

<210> SEQ ID NO 84
<211> LENGTH: 11
<212> TYPE: PRT
<213> ORGANISM: Artificial Sequence
<220> FEATURE:
<223> OTHER INFORMATION: VarID: chr8_56698861_A>T

<400> SEQUENCE: 84

Lys Tyr Leu Val Glu Ile Val Gln Glu Ser Trp
1               5                   10

<210> SEQ ID NO 85
<211> LENGTH: 21
<212> TYPE: PRT
<213> ORGANISM: Artificial Sequence
<220> FEATURE:
<223> OTHER INFORMATION: VarID: chr1_209849154_T>G

<400> SEQUENCE: 85

```
Lys Met Val Lys Leu Tyr Val Leu Gly Ser Val Ala Leu Phe Gly
1               5                   10                  15

Val Val Leu Gly Arg
            20

<210> SEQ ID NO 86
<211> LENGTH: 22
<212> TYPE: PRT
<213> ORGANISM: Artificial Sequence
<220> FEATURE:
<223> OTHER INFORMATION: VarID: chr1_209849154_T>G

<400> SEQUENCE: 86

Ala Leu Phe Gly Val Val Leu Gly Arg Met Glu Thr Val Cys Ser Pro
1               5                   10                  15

Phe Thr Ala Ala Arg Arg
            20

<210> SEQ ID NO 87
<211> LENGTH: 22
<212> TYPE: PRT
<213> ORGANISM: Artificial Sequence
<220> FEATURE:
<223> OTHER INFORMATION: VarID: chr17_28511815_G>T

<400> SEQUENCE: 87

Asp Glu Ile Glu Glu Thr Arg Val Asn Phe Arg Arg Glu Lys Val Ile
1               5                   10                  15

Glu Thr Pro Glu Asn Asp
            20

<210> SEQ ID NO 88
<211> LENGTH: 23
<212> TYPE: PRT
<213> ORGANISM: Artificial Sequence
<220> FEATURE:
<223> OTHER INFORMATION: VarID: chr17_72832365_C>T

<400> SEQUENCE: 88

Met Tyr Thr Leu Asn Phe Ala Cys Cys Asp Val Val Gly Leu Ala Ala
1               5                   10                  15

Val Arg Phe Phe Leu Gly Leu
            20

<210> SEQ ID NO 89
<211> LENGTH: 18
<212> TYPE: PRT
<213> ORGANISM: Artificial Sequence
<220> FEATURE:
<223> OTHER INFORMATION: VarID: chr2_74328527_G>A

<400> SEQUENCE: 89

Ser Thr Ser Ala Leu Ala Gly Pro Ser Leu Thr Glu Lys Pro Trp Ala
1               5                   10                  15

Leu Arg

<210> SEQ ID NO 90
<211> LENGTH: 22
<212> TYPE: PRT
<213> ORGANISM: Artificial Sequence
<220> FEATURE:
<223> OTHER INFORMATION: VarID: chr6_88769199_C>A

<400> SEQUENCE: 90
```

Lys Tyr Met Trp Lys Leu Leu Arg Gln Asp Gln Gln Ser Ile Ile Leu
1               5                   10                  15

Val Asn Asp Ser Glu Ile
            20

<210> SEQ ID NO 91
<211> LENGTH: 23
<212> TYPE: PRT
<213> ORGANISM: Artificial Sequence
<220> FEATURE:
<223> OTHER INFORMATION: VarID: chr17_28511815_G>T

<400> SEQUENCE: 91

Asp Asp Glu Ile Glu Glu Thr Arg Val Asn Phe Arg Arg Glu Lys Val
1               5                   10                  15

Ile Glu Thr Pro Glu Asn Asp
            20

<210> SEQ ID NO 92
<211> LENGTH: 13
<212> TYPE: PRT
<213> ORGANISM: Artificial Sequence
<220> FEATURE:
<223> OTHER INFORMATION: VarID: chr1_209849154_T>G

<400> SEQUENCE: 92

Arg Met Glu Thr Val Cys Ser Pro Phe Thr Ala Ala Arg
1               5                   10

<210> SEQ ID NO 93
<211> LENGTH: 15
<212> TYPE: PRT
<213> ORGANISM: Artificial Sequence
<220> FEATURE:
<223> OTHER INFORMATION: VarID: chr2_165984466_C>T

<400> SEQUENCE: 93

Lys Met Gln Glu Cys Phe Gln Lys Ala Phe Phe Arg Lys Pro Lys
1               5                   10                  15

<210> SEQ ID NO 94
<211> LENGTH: 8
<212> TYPE: PRT
<213> ORGANISM: Artificial Sequence
<220> FEATURE:
<223> OTHER INFORMATION: VarID: chr10_24896718_G>T

<400> SEQUENCE: 94

Lys Thr Ser Ala Pro Leu Ile Arg
1               5

<210> SEQ ID NO 95
<211> LENGTH: 20
<212> TYPE: PRT
<213> ORGANISM: Artificial Sequence
<220> FEATURE:
<223> OTHER INFORMATION: VarID: chr1_209849154_T>G

<400> SEQUENCE: 95

Met Val Lys Leu Tyr Val Leu Gly Ser Val Leu Ala Leu Phe Gly Val
1               5                   10                  15

Val Leu Gly Arg
            20

<210> SEQ ID NO 96

```
<211> LENGTH: 23
<212> TYPE: PRT
<213> ORGANISM: Artificial Sequence
<220> FEATURE:
<223> OTHER INFORMATION: VarID: chr1_209849154_T>G

<400> SEQUENCE: 96

Val Leu Ala Leu Phe Gly Val Val Leu Gly Arg Met Glu Thr Val Cys
1               5                   10                  15

Ser Pro Phe Thr Ala Ala Arg
            20

<210> SEQ ID NO 97
<211> LENGTH: 15
<212> TYPE: PRT
<213> ORGANISM: Artificial Sequence
<220> FEATURE:
<223> OTHER INFORMATION: VarID:   chr17_28511815_G>T

<400> SEQUENCE: 97

Val Asn Phe Arg Arg Glu Lys Val Ile Glu Thr Pro Glu Asn Asp
1               5                   10                  15

<210> SEQ ID NO 98
<211> LENGTH: 23
<212> TYPE: PRT
<213> ORGANISM: Artificial Sequence
<220> FEATURE:
<223> OTHER INFORMATION: VarID: chr17_28511815_G>T

<400> SEQUENCE: 98

Ala Asp Asp Glu Ile Glu Glu Thr Arg Val Asn Phe Arg Arg Glu Lys
1               5                   10                  15

Val Ile Glu Thr Pro Glu Asn
            20

<210> SEQ ID NO 99
<211> LENGTH: 15
<212> TYPE: PRT
<213> ORGANISM: Artificial Sequence
<220> FEATURE:
<223> OTHER INFORMATION: VarID: chr2_74328527_G>A

<400> SEQUENCE: 99

Ala Leu Ala Gly Pro Ser Leu Thr Glu Lys Pro Trp Ala Leu Arg
1               5                   10                  15

<210> SEQ ID NO 100
<211> LENGTH: 12
<212> TYPE: PRT
<213> ORGANISM: Artificial Sequence
<220> FEATURE:
<223> OTHER INFORMATION: VarID: chr1_209849154_T>G

<400> SEQUENCE: 100

Ser Val Leu Ala Leu Phe Gly Val Val Leu Gly Arg
1               5                   10
```

RANKING SYSTEM FOR IMMUNOGENIC CANCER-SPECIFIC EPITOPES

CROSS REFERENCE TO RELATED APPLICATION

The present application claims priority to U.S. Provisional Application Ser. No. 62/479,320, filed on Mar. 31, 2017, and PCT Application Serial No. PCT/US18/25597, filed on Mar. 31, 2018, which are hereby incorporated by reference in their entirety.

SEQUENCE LISTING

The instant application contains a Sequence Listing which has been submitted electronically in ASCII format and is hereby incorporated by reference in its entirety. Said ASCII copy, created Sep. 22, 2019, is named "ACTG-1PCT-1US_SeqList_ST25.txt" and is 23,039 bytes in size.

FIELD

This disclosure relates to systems and methods that identify, predict and rank immunogenic T cell epitopes. It is related to field of genomics, next-generation sequencing, immuno-oncology, and precision medicine.

BACKGROUND

Stimulating immune response against tumor cells by employing tumor-specific antigens has led to prominence in fighting cancer. These antigens have been determined as the link between tumor genomics and clinical benefit in immunotherapy. Briefly, genes harboring cancer mutations give rise to peptides carrying the mutation. These peptides subsequently bind to the major histocompatibility complexes (MHCs) Class I and II, and are presented onto the tumor cell surface as antigens. The immune system, particularly cytotoxic T cells and helper T cells, may recognize these antigens as non-self and trigger immune responses. Many of these antigens are exclusive to the tumor and are previously unseen by the immune system. Therefore, they serve as a suitable target for immunotherapy, where the treatment would home in on the tumor cells without damaging normal cells.

Eliciting T-cell response using tumor-specific antigens has met with variable results. Utilizing these antigens faced two obstacles: first, immune cells must recognize these antigens as non-self and elicit immune responses without attacking normal cells; second, even if the T cells recognize the antigens as non-self, cells in our body, including mutated tumor cells, possess safe checks known as immune checkpoints, which prevents T cells from long-term, high amplitude attacks. These immune checkpoints need to be made dysfunctional for successful immunotherapy. The second obstacle has come under the spotlight in recent years. Inhibitors to these immune checkpoints, such as anti-PD1, anti-PDL1, and anti-CTLA4 antibodies, were developed, followed by a growing number of drugs, clinical trials, and target cancer types. Nevertheless, there is still substantial room for improvements, as the response rate of the immune checkpoint inhibitor treatment is approximately 20% or lower. It is thus ideal to select patients who would be sensitive to immunotherapy prior to treatment. Possession of high quantity or high qualitied tumor-specific antigens have been suggested to be highly relevant to treatment response and survival rate. An accurate identification of these antigens is in high demand to facilitate patient selection in administering immune checkpoint inhibitors.

In contrast, progresses that directly exploits the selection of antigens for T-cell recognition remains relatively stagnant. T cells elicit attacks after recognizing antigens foreign. However, effective approaches for T-cell recognition of tumor-specific antigens is currently lacking. Therapeutic approaches could be collectively grouped into cancer vaccination and adoptive cell transfer. Therapeutic cancer vaccination aims at delaying tumor progression and promoting tumor regression by enlarging the T cells from a naïve repertoire and reactivating existing T cells. The vaccine is composed of the said tumor-specific antigens, where these antigens are selected for their ability to stimulate immune responses. However, advancement of vaccines has been hindered by suboptimal selection of immunogenic antigens, leaving the vaccines ineffective. Adoptive cell transfer directly focuses on training the immune cells to attack tumor cells. The immune cells, typically T cells or dendritic cells, are collected from the patient and trained in a laboratory. The T cells that successfully eliminate tumor cells through recognizing tumor-specific antigens are reinfused back to the patient, where the T cells would attack tumor cells in the patient. However, this approach is also plagued by ineffective antigen selection, leading to a low success rate. As shown in both approaches, optimal selection of immunogenic tumor-specific antigens is necessary for achieving clinical benefit in immunotherapy.

A reliable method to accurately identify immunogenic tumor-specific antigens would be widely applicable and crucially beneficial to the various immunotherapy strategies. Current identification of tumor-specific antigens generally consists of identifying a mutation and predicting binding affinity of MHC to epitopes, the antigenic determinant portion of the antigen. Multiple epitope prediction tools exist with inconsistent results, and subsequent experiments only validated approximately 55% of the predicted epitopes (Rajasagi M et al., Blood. 2014 Jul. 17; 124(3):453-62.) Typical methods are based on the peptide sequences, without simultaneous consideration of both classes of MHCs and their corresponding immune cells. Furthermore, each patient or sample has specific characteristics that impact predictions, and these sample-specific characteristics have not been incorporated in current neoantigen ranking methods. These characteristics can be collectively named dosage of alleles. A high dosage in the mutated alleles and the MHC alleles lead to discernably higher chances of tumor-specific antigens being recognized by the immune system, and hence affects the epitope predictions. This disclosure describes systems and methods that accurately identify, predict, and rank immunogenic epitopes using both peptide-level information and sample-level information. Peptide-level information simultaneously integrates MHC Class I and II presentation, CD4 activation and CD8 activation, while sample-level information includes dosage of alleles, namely clonality of mutated alleles and number of MHC alleles. Moreover, the systems and methods incorporate a comprehensive list of factors, each based on crucial components in the cellular processes, tumor-specific characteristics, antigen presentation processes, and immune activation processes. Optimal selection of epitopes with weights on each factor is disclosed. The disclosure also describes epitope ranking methods for further development in personalized treatment such as using cancer vaccine, adoptive cell transfer, or immune checkpoint inhibitors.

SUMMARY

The present disclosure describes systems and methods that identify, predict, and rank epitopes derived from a disease tissue of an individual, wherein said epitopes would elicit immune responses against the disease in said individual. The system simultaneously considers peptide-level information and sample-level information. Peptide-level information includes computations on various components, comprising the epitope sequences related to MHC Class I, MHC Class II, helper T cell activation, and cytotoxic T cell activation. Sample-level information are tumor-specific factors, including clonality of mutated alleles, and number of MHC alleles. The identification systems and methods integrate said factors, and designate weights to the factors wherein the weights represent the magnitude of contribution of said factors in eliciting immune response. An immunogenic score is given to the epitopes. The present disclosure also provides systems and methods to rank the epitopes. The ranking system and method prioritize epitopes particular to the individual, wherein the epitopes can be utilized for a personalized treatment of the disease.

The system is provided with variant information as a list of mutations and copy number variations, wherein the variants are identified using a next generation sequencing platform. Along with the variants, the relevant sequencing information are also provided, including raw reads of the sequencing results. The system is also provided with the types of major histocompatibility complex (MHC) to be associated with the mutations. In some embodiments, the types of MHC are of a single individual whom may or may not have provided the mutations. The system would output a set of mutation-associated epitopes comprising a) the peptide sequences containing the mutation; b) a peptide-level score for each epitope, wherein the score represents the capability of the peptide to be presented and activate immune response; c) a sample-level score for each epitope, wherein the score represents mutation clonality in heterogeneous tumors; and d) a rank for each epitope, wherein the rank prioritizes epitopes that is predicted to be effective for immunotherapy treatment.

The systems and methods of present disclosure comprise several or all of the following steps: 1) determining the characteristics of the mutations based on next generation sequencing data, including variant calling, annotation, copy number detection, loss-of-heterozygosity, and tumor purity; 2) determining the characteristics of the genes harboring the mutations; 3) determining expression of the genes, wherein expression is based on tissue-specific and disease-specific data on public available repositories; 4) determining protein abundance of the genes, wherein abundance is based on tissue-specific and disease-specific data on public available repositories; 5) obtaining the peptide sequences containing the mutation. For MHC Class I, the peptides are 8-15 amino acids in length, preferentially 8-11 amino acids in length. For MHC Class II, the peptides are 9-23 amino acids in length; 6) predicting the binding of the peptides to MHC class I and class II; 7) predicting activation of immune response of the peptides to CD4+ and CD8+ T cells; 8) predicting the peptides would undergo proper antigen presentation process; 9) comparing the peptides with their unmutated counterparts; 10) comparing the peptides with known antigens; 11) determining dosage of MHC Class I allele, and incorporate into the MHC Class I computation; 12) incorporating and integrating the factors in in steps 1-11 for weight assignment and immunogenicity prediction at the peptide level; 13) computing the clonal mutation frequency for sample-level score; 14) conglomerating peptide-level score and sample-level score as an immunogenic score; 15) determining copy number loss of the genes, wherein a losing all copies of the gene would render an immunogenic score as low as 0; 16) ranking the peptides based on the immunogenicity.

Immunogenicity of the epitopes is based on one, more than one, or any combination of the following factors including but not limited to, i) variant frequency, ii) copy number alteration, iii) loss-of heterozygosity, iv) tumor purity, v) clonality of mutated allele, vi) homology with known antigen sequence (antigen homology), vii) similarity with wildtype (self-similarity) for MHC Class I, viii) similarity with wildtype (self-similarity) for MHC Class II, ix) gene expression, x) protein abundance, xi) proteasome cleavage, xii) TAP transport, xiii) MHC Class I binding affinity, xiv) MHC Class II binding affinity, xv) MHC Class I binding stability, xvi) dosage of MHC Class I allele, and xvii) Peptide similarity to the consensus sequence matrix of immunogenic T cell epitopes.

In some embodiments, the individual contains a higher dosage of MHC alleles, wherein a higher dosage means the individual carries a homozygous pair of MHC alleles, one from each parent. Higher dosage of MHC alleles may lead to an added effect in antigen presentation. The effect of allele dosage is added into the MHC Class I computation of the model.

For peptide-level score, four machine learning models are constructed using factors from vi to xv. Model I predicts MHC Class I presentation, incorporating gene expression, protein abundance, proteasome cleavage, TAP transport, MHC Class I binding affinity, MHC Class I binding stability, and dosage of MHC alleles. Model II predicts MHC Class II presentation, incorporating MHC Class II binding affinity. Both models are trained using data that measured MHC-peptide binding by mass spectrometry. Model III predicts helper T cell activation, incorporating self-similarity and antigen homology. Model IV predicts cytotoxic T cell activation, incorporating self-similarity, antigen homology and MHC Class I immunogenicity. Models III and IV are trained using in vitro T cell immune response assay results. Machine learning regressors and analytical methods are used to integrate any of these four models and combinations thereof. The factors in the final model are weighted in the system of feature selection and machine learning model with iterative model tuning for optimization, and the model is validated with known immunogenic epitopes.

For sample-level score, factors i to v are considered. These factors are analytically calculated to determine whether the said mutation is a clonal mutation. Tumors may contain multiple subclones, where each subclone is of a distinct genetic makeup. Clonal mutations are defined as mutations that appear in majority of the clones. In other words, these mutations occur early in the 'trunk' of cancer mutation evolution. A tumor-specific antigen derived from a clonal mutation is presented in majority of the tumor cells, and hence posed as a likely target for immune attack. Conversely, a tumor-specific epitope derived from a mutation of a small subclone is a "leaf" mutation, and is only presented in a fraction of the tumor cell. Even if these tumor cells are attacked, other clones remain unaffected. Clonal mutations are determined by calculating the number of mutated allele based on maximum likelihood of expected allele frequency, and then using the number of mutated allele to estimate subclonal purity. The sample-level score is calculated from the subclonal purity and tumor purity.

The immunogenic score incorporates both the peptide-level score and sample-level score. The immunogenic scores for each peptide is then ranked as the final output of the integrated identification system.

BRIEF DESCRIPTION OF THE DRAWINGS

FIG. 6. Immune response comparison by antigen presentation information and both T-cell features. A) Example 11 considering Example 5 and Example 6. B) Example 12 considering Example 7 and Example 8. C) Example 13 considering Example 9 and Example 10.

DETAILED DESCRIPTION

Figure 1:
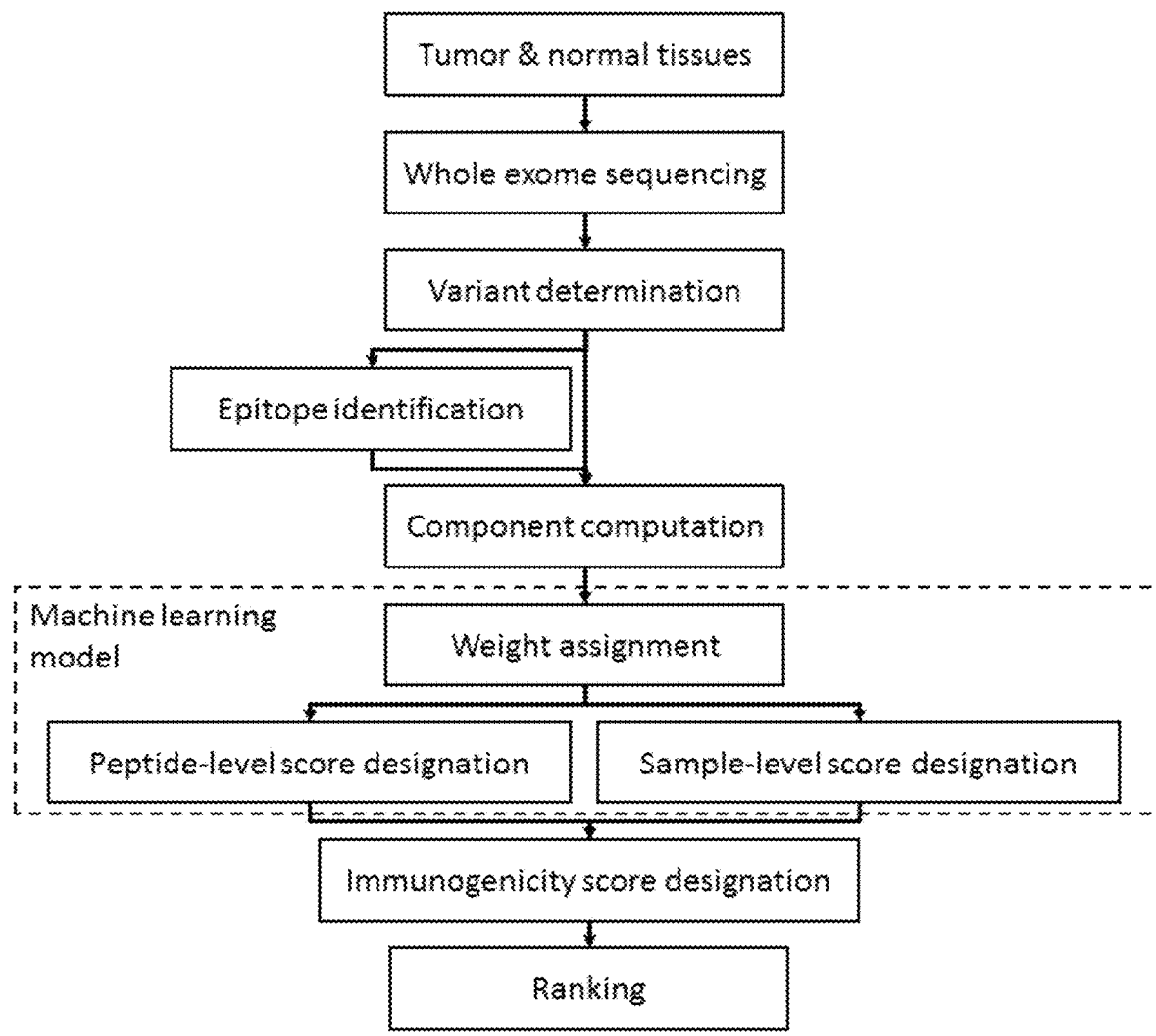
FIG. 1. Flow chart of the system. Describes the overall process and each major step in the system.

In some embodiment, the present disclosure describes an integrated systems and methods that identify disease-specific epitopes, predict the immunogenicity of the epitopes, and rank the epitopes for further personalized treatment of an individual in the grand scheme of precision medicine. The systems and methods integrate sequence-based variant calling, sequence-based copy number determination, sequence alignment, similarity matrix, machine learning, optimization, and mathematical modeling for an accurate and practical identification of immunogenic epitopes (FIG. 1). The systems and methods consider each component that assembles cellular processes, tumor-specific characteristics, antigen presentation processes, and immune activation processes. The components in each process are computed as factors by following their actual functions in the cell. Each factor is weighted according to the magnitude of contribution to the immunogenicity of the epitopes. A weighted factor allows investigations into the reasons of being immunogenic and in term would facilitate investigation in both clinical and research settings. The factors represent peptide-level information and sample-level information, which are all considered by the system, wherein the system would utilize these factors to score the immunogenicity of the epitopes. The present disclosure also provides a scheme to rank the identified epitopes. The ranking is based on the predicted immunogenic score of the epitopes.

The terminologies used in the disclosure should be understood for the purpose of describing the embodiments and claims. It should be understood that any change in the tenses and word stems of the terminologies should not limit this disclosure. It should also be understood that the any synonymous term of the terminologies as commonly understood should not be used to limit this disclosure.

The disclosure is not limited to a specific methodology, protocol, or procedure described herein, as these may vary. The specific embodiments described herein are simply examples, and should not be construed to limit the scope of the disclosure.

As used in this disclosure, the singular forms "a," "an," and "the" specifically also encompass the plural forms of the terms to which they refer, unless the content clearly dictates otherwise.

The term "component" refers to a specific characteristic in the mutation, a specific characteristic in the gene, a specific step in the cellular process, or a specific characteristic of the sample.

The term "factor" refers to a computed representation of a factor, wherein a factor may be calculated by a formula, predicted by a computational tool, or stratified as a category.

The term "peptide" refers to an amino acid sequence of various length, may or may not be immunogenic, and may or may not be tumor-related. The term "antigen" refers to a peptide that is immunogenic and can be recognized by the immune system. The term "epitope" refers to a short antigen that can be presented to the surface of a cell. Said epitope may be generated through proteasome cleavage of a longer antigen.

The term "cancer vaccine" refers to the therapeutic vaccines, which aims to treat a cancer by enhancing the body's immune system against the cancer. It is not to be confused with the commonly administered preventive vaccine, which is administered prior to the disease for prevention.

The term "major histocompatibility complex" and its abbreviation "MHC" refers to any variations and names of the MHC, including but not exclusive to its classes, alternative names such as human leukocyte antigen (HLA), types such as A, B, C, DRB1, DPA1, DPB1, DQA1, DQB1 and so on.

The term "mutation", unless otherwise specified, refers to nonsynonymous somatic mutations, comprising missense mutations, frameshift mutations, and splice site mutations. The term "variant" includes mutations, but further includes structural variations, comprising copy number variations, chromosomal rearrangements, fusions, translocations, and inversions. Somatic variants are defined as variants that were not present in the germline and occurred later in life, particularly during cancer development. These variants may lead to tumorigenesis or are passengers that go along with cancer.

The term "total depth" refers to the total number of reads being sequenced at a specific position in the gene.

Figure 2:
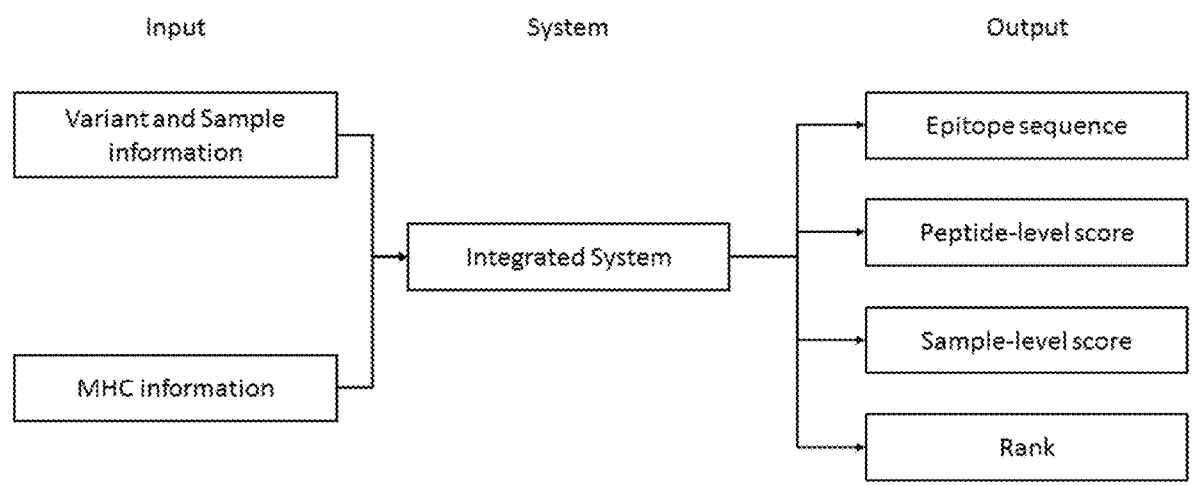
FIG. 2. Input and output. The system takes variant and sample information produced from a next generation sequencing platform as input. It also takes MHC information. The system outputs the amino acid sequence, peptide-level score, sample-level score, and a rank of the immunogenic epitopes.

In some embodiments, the system or method takes NGS sequencing data as input (FIG. 2). NGS data can be in variant call format (VCF), sequence alignment map (SAM), binary alignment map (BAM), FASTQ, or other raw or processed file formats. The VCF file contains information about a position in the genome. The information includes, but not exclusive to the mutated allele, the reference allele, the chromosome, a chromosomal position, allele frequency and total depth. In some embodiments, the user should also provide information derived from changes in large segments of an allele, including copy number variation, tumor purity, and loss of heterozygosity. In some embodiments, the system takes in a SAM/BAM file, where the aforementioned data can all be computed from the SAM/BAM file. In some embodiments, the system takes in a FASTQ file, where the aforementioned data can be computed after performing sequence alignment to a reference genome.

The system also takes the type of MHC as input (FIG. 2). In some embodiments, the MHC Class I is of supertypes including but not limited to A, B, and C, and is typed with a resolution of at least four digits. In some embodiment, the MHC Class II is of supertypes including but not limited to DRB1, DPA1, DPB1, DQA1, DQB1, and is typed with a resolution of at least four digits. In some embodiment, the MHC type can be obtained from the NGS data described herein.

The present disclosure describes identification of the epitope and prediction of its immunogenicity, and is based on one, more than one, or any combination of the following factors: i) variant frequency of the mutation as determined by variant calling, ii) copy number alteration, iii) loss-of heterozygosity (LOH) for the mutation iv) tumor purity, v) clonality of the mutated allele, vi) homology with known antigen as determined by sequence alignment, vii) similarity with wildtype peptide as determined by the ratio of MHC binding affinity between mutated and wildtype peptide for MHC Class I, viii) similarity with wildtype peptide as determined by the ratio of MHC binding affinity between mutated and wildtype peptide for MHC Class II, ix) gene expression as determined from tissue-specific and diseases-specific experiments, which can be obtained from public databases, x) protein abundance as determined from tissue-specific and diseases-specific experiments, which can be obtained from public database, xi) proteasome cleavage as determined by proteasome degradation data, xii) TAP transport as determined by transport rate data, xiii) MHC Class I binding affinity as determined by in vitro binding assays, xiv) MHC Class II binding affinity as determined by in vitro binding assays, xv) MHC Class I binding stability, xvi) dosage of MHC Class I allele, xvii) MHC Class I immunogenicity as determined by in vitro or ex vivo T cell expansion assays.

An epitope appears on the surface of cells through the antigen presentation process. In the case of cancer-specific epitopes, genetic mutations derive mutated peptides, the mutated peptides is then be cleaved by proteasome into short epitopes, and then transported in to endoplasmic reticulum through the TAP protein. Inside the endoplasmic reticulum, the epitope binds to the MHC complex. Then, together with the MHC complex, the epitope is presented on the cell surface for immune cell recognition. Each step in this antigen presentation process contributes to the immunogenicity of the epitope.

Mutations in a tumor may not occur in every single tumor cell. If a mutation that derives an immunogenic epitope occurs in a larger portion of the tumor cells, then the immune cells are more likely to wipe out the tumor as they recognize most of the tumor cells as targets. Therefore, the percentage of mutations detected in the tumors, as represented by a variant frequency of 0 to 100% is an important aspect in determining the immunogenicity of the epitope. A higher variant frequency represents the mutation may be in a larger proportion of the tumor and hence may impact the effectiveness of immune cell attack. Similarly, other characteristics of the mutation, including copy number alteration, loss of heterozygosity (LOH), tumor purity and clonality of the mutated allele, reflect the proportion of the tumors cells that produces the mutated epitope, which may lead to immune cell attack.

The genes that the epitopes originate from needs to be expressed. Gene expression in tumor samples can be measured using NGS (ex: RNA-seq), microarray, quantitative real-time PCR, or Northern blots. Tissue and cancer-specific gene expressions can also be obtained from public available databases. Utilizing data from public available databases allows determination of genes that are truly expressed. Current understanding of gene expression is that the genome is pervasively transcribed. Even though the transcription regulation process is complicatedly and intricately controlled, low amounts of expression are still detected and less regulated. Hence, much noise is present in individualized gene expression data. If a gene is expressed in the same tissue across various individuals with the same disease, it indicates the gene is generally transcribed in the cell type. The genes need to be expressed so translation would occur for epitope formation. In some datasets, gene expression is qualitatively determined as low, medium, high, or none. In these datasets, gene expression values can be transformed into numeric values such as 0, 1, 2, and 3. In other datasets, gene expression can be a numeric value with various units, such as ratio or arbitrary units. In some embodiments, the model takes a numeric value or a transformed numeric value into the integrated machine learning model. A gene that is not expressed is represented as low, 0 or none. In another embodiment, the system filters out the genes that are not expressed. Conversely, a gene expression that is considered high by each respective expression detection methods contributes to the quantity of the epitope. An epitope with a high quantity has a higher chance to encounter the MHC complex and hence is more likely to be presented.

Similarly, protein abundance information can be measured by mass spectrometry, immunofluorescence, immunohistochemistry or Western blots. Protein abundance data can also be obtained from public domains. The quantity of the protein harboring the tumor-specific epitope helps determining the possibility of epitope binding to MHC. An epitope could be very highly immunogenic but in low quantities. Under this situation, the epitope is not affective in eliciting immune responses. In some datasets, protein abundance is qualitatively determined as low, medium, high, or none. In these datasets, protein abundance values can be transformed into numeric values such as 0, 1, 2, and 3. In other datasets, protein abundance can be a numeric value with various units, such as ratio or arbitrary units. In some embodiments, the model takes a numeric value or a transformed numeric value into the integrated machine learning model. A protein that is not expressed is represented as low, 0 or none. In another embodiment, the system assigns a zero in its score related to protein abundance or filters out the proteins that are not expressed. Conversely, a protein abundance that is considered high by each respective abundance detection methods contributes to the quantity of the epitope. An epitope with a high quantity has a higher chance to encounter the MHC complex and hence is more likely to be presented.

Similarity of mutated peptide to the unmutated wildtype peptide is determined. If a mutated peptide is similar to a wildtype peptide, it may be recognized as self and be tolerated by T cells. The similarity of a mutated peptide to its unmutated wildtype sequence can be calculated using the difference in their binding affinities to MHC. The difference is translated into a numerical measure of difference, where the ratio of binding affinity of the mutated peptide to the wildtype peptide is calculated for both MHC class I and class II.

Homology of the mutated peptide to a known antigen is determined. Known antigens are derived from bacteria, viruses and other pathogens, where T cells would normally elicit immune responses. Therefore, a mutated peptide being very similar to a known antigen are more likely to elicit immunogenicity. Antigen homology is determined through sequence alignment of the mutated peptide to all known antigens, wherein the identity of the sequence and the length of the identity is considered. Homology can be determined as the percentage of the mutated peptide containing the same sequence as the antigen.

An epitope encounters the MHC complex in the endoplasmic reticulum. To be inside the endoplasmic reticulum, the mutated peptide must be cleaved into an epitope of suitable length by the proteasome. Sites in the peptide that may be cleaved by a proteasome is predictable as a score of 0 to 1. It is preferable that there are minimal, or 0, cleavable sites within an epitope, as an epitope likely to be cleaved may be degraded before presentation. Then the epitope must be transported into endoplasmic reticulum by the TAP protein. Transport efficiency of the epitope through TAP is represented as an IC50 value, where a lower IC50 indicates better transport. An epitope that is easily transported have higher chances of encountering the MHC complex.

The epitope needs to bind to the MHC complex for presentation. MHC Class I may bind to epitopes of 8 to 15 amino acids or longer, but preferably 8 to 11 amino acids. MHC Class II may bind to epitopes of 9 to 23 amino acids or longer, but preferably 15 and 16 amino acids. The epitope anchors on the MHC with positions specific to each type of MHC. The specific amino acids on these anchor positions are crucial to presentation as they indicate the affinity of binding, however amino acids in other positions also affect binding affinity. A strong MHC binding affinity for both class I and class II, as indicated by an IC50 of less than 1500 nM or 1000 nM, preferably less than 500 nM, represents that the epitope likely binds to the MHC complex and be presented on the surface of the cells.

In addition to binding affinity, the stability of the epitope binding to MHC is also crucial in antigen presentation. An epitope may have a very strong affinity with the MHC complex, but the time it stays bounded to the MHC is not long enough for presentation. If an epitope dissociates with MHC complex before presentation, the said epitope will not show up on the cell surface. MHC binding stability, as denoted by a half-life score of 0 to 1, represents the time the epitope stays bounded to MHC. Staying bounded for a longer period of time increases the likelihood of the epitope being presented on the surface of the cell.

MHC Class I immunogenicity represents the ability of specific composition of the epitope sequence in eliciting immune response. Specific epitope sequence may have biochemical impact on the activation T-cell receptor (TCR) of a cytotoxic T-cell. Triggering the TCR is the first step in a T-cell attack. A high MHC Class I immunogenicity as represented by a score ranging from −1 to 1 indicates T cells may expand upon contacting with said epitope.

Some individuals possess the same type of MHC alleles from both parents, namely a homozygous pair of MHC. Homozygous MHC alleles may lead to an added effect due to allele dosage. Homozygous MHC alleles increases the quantity of alleles to be bound by potential epitopes, and hence discernably increases the likelihood of presenting the epitope to cell surfaces. Moreover, high quantity of MHCs on cell surfaces also increases the likelihood of T-cells recognizing the epitope. Therefore, an added effect is considered in the computation of MHC Class I.

According to any of the methods above that involves using immune response information from individuals under immunotherapy treatment, the lack of immune response may be due to defects in a participant in the antigen presentation machinery. These defects would falter the antigen presentation pathway, leading to epitopes not being presented to the surface of the cell despite the epitopes are immunogenic. These situations are presented as confounding factors in determining the reasons for response to immunotherapy. Therefore, individuals with defects in antigen presentation machinery are not considered.

According to any one of the method described above, each factor is weighted based on the identification system, wherein the identification system comprises feature selection, machine learning, validation, and iterative model tuning for optimization (FIG. 1). The features used after feature selection are listed as, Peptide-Level Features MHC I presentation: gene expression, protein abundance, proteasome cleavage, TAP transport, MHC Class I binding affinity, MHC Class I binding stability MHC II presentation: MHC Class II binding affinity Helper T cell activity: self-similarity, antigen homology Cytotoxic T cell activity: self-similarity, antigen homology, MHC Class I immunogenicity Sample-Level Features Clonality of Mutated Alleles, Dosage of MHC Class I Allele For peptide-level score, four models, MHC Class I, MHC Class II, helper T cell activation, and cytotoxic T cell activation, using the respective features are constructed. Additionally, MHC Class I incorporates a sample-level feature, dosage of MHC Class I allele into its model. A combination of machine learning regressors are used to integrate any of these four models and combinations thereof. The peptide-level model is trained with iterative model tuning for optimization, and the model is validated with known immunogenic epitopes. Any two or more machine learning regressors are then integrated with mathematical and analytical methods, such as multiplication, to obtain the final peptide-level score.

For sample-level score, clonality of mutated allele is calculated. A clonal mutation or 'trunk mutation' is defined as a mutation that occurred during the early stages of the tumor development, and hence it belongs to the trunk in a tree of cancer mutation evolution as opposed to the mutations occurring at the branches. Clonal mutations generally exist in most of the clones of the tumor. Determination of clonal mutation is based on assigning an expected number of mutated allele based on statistical significance of expected allele frequency and observed allele frequency, and then using the number of mutated allele to estimate subclonal purity. The portion of subclonal purity and tumor purity is the sample-level score.

The immunogenic score is the integration of peptide-level score and sample-level score.

The model is tuned through multiple iterations of parameter tuning, where the model is re-constructed and trained multiple times, each iteration would change selected features or weights. The model with the best performance is the final model. An immunogenic score is given to each epitope.

The order of the magnitude of immunogenic score represents the rank of each tumor-specific epitope computed by the integrated system.

Machine learning methods are used in the models described above, including the models for MHC class I presentation, MHC class II presentation, helper T cell activation, cytotoxic T cell activation, and the integration or these models together with sample-level scores to arrive at a final immunogenic score. There are several machine learning methods that are suitable for training these models, such as regression-based models, tree-based models, Bayesian models, support vector machines, boosting models, and neural network-based models.

The disclosed system and method is beneficial in the field of immune-oncology. It provides an approach to facilitate the treatment of diseases for an individual. The immunogenic epitopes identified from the system and method is determined for each individual and provides an approach for personalized or individualized medicine. The system provides a set of immunogenic epitopes that can be employed in various immunotherapy strategies. The integrated system of epitope identification, immunogenicity prediction and epitope ranking is useful for patients who are considering immunotherapy, such as checkpoint inhibitors, cancer vaccine, or adoptive cell transfer. In cancer vaccine and adoptive cell transfer, the ranked epitopes serve as a selected set of highly promising candidates for vaccine synthesis or immune cell training. In immune checkpoint inhibitor therapy, the number of immunogenic epitopes serves a reliable source of response prediction for administering the drug. The present system is suitable for practicing precision medicine on an individual or a general population with the disease.

EXAMPLES

Example 1. Prediction of Peptide Presentation by MHC Class I Complex by Considering the Peptide Binding Affinity and Binding Stability to MHC Class I Complex In order for a peptide to be an antigen, it needs to be able to be presented to the surface of a cell by the MHC complex to be recognized by immune cells. This process includes peptide presentation by MHC class II complex in antigen presentation cells to present the peptide to CD4+ T cells, peptide presentation by MHC class I complex in antigen presentation cells to present the peptide to CD8+ T cells and peptide presentation by MHC class I complex in tumor cells to CD8+ T cells. In this example, we built a model with selected features to predict peptide presentation by MHC class I complex.

We built a model to predict MHC class I presentation by considering two properties affecting the peptide binding to MHC class I complex, the binding affinity and binding stability of peptides. We calculated the binding affinity (IC50) of a peptide to MHC class I complex using NetMHC4.0 (Andreatta M and Nielsen M, Bioinformatics (2016) February 15; 32(4):511-7; Nielsen M, et al., Protein Sci., (2003) 12:1007-17). For HLA complex that were not available in NetMHC4.0, we used NetMHCpan3.0 (Nielsen M and Andreatta M, Genome Medicine (2016): 8:33; Hoof I, et al., Immunogenetics 61.1 (2009): 1-13). We calculated the stability for peptide binding to MHC class I complex using NetMHCstabpan1.0 (Rasmussen M, et al., J Immunol. 2016 Aug. 15; 197(4):1517-24). We trained a machine learning model using the data collected from Bassani-Sternberg et al., Molecular & Cellular Proteomics, 2015 and Bassani-Sternberg et al., Nature Communications, 2016 as training data. The peptide sequences which are generated from more than one gene, not labeled as unmodified sequence, and those whose lengths are not between 9 and 11 are removed from the training data. The peptides and corresponding HLA types which are identified as presented peptide-HLA complexes were used as positive training data. The same peptide sequences paired with other HLA types were considered negative training data. The binding affinity and stability of each peptide to their corresponding HLA type were calculated as described above. A logistic regression model was built with the peptide binding affinity and binding stability to MHC class I complex as features and using LogisticRegression in Scikit-learn (Fabian Pedregosa et al., JMLR (2011) Oct. 12: 2825-2830) to predict peptide presentation by MHC class I. A ten-fold cross-validation was performed and the accuracy and area under the receiver operation curve (AUC of ROC) for the testing dataset of the training data are listed in Table 1. In this model, we found that the binding affinity contributes more strongly than binding stability.

Example 2. Prediction of Peptide Presentation by MHC Class I Complex by Considering the Peptide Binding Affinity and the Gene Expression Level Besides the ability of peptides to bind to MHC class I complex, it is also important that a peptide is expressed so that it can be presented. In this example, we built a model to predict peptide presentation by MHC class I complex by accounting for gene expression and the peptide binding ability to MHC class I complex.

We calculated the binding affinity of a peptide to MHC class I complex as described in Example 1. The gene expression level for a peptide is calculated as the RNA expression level of the gene generating the peptide. We obtained the gene expression level for peptides using the Illumina Body Map (Petryszak R et al., Nucleic Acids Res. 2016 Jan. 4; 44(D1):D746-52). We trained a machine learning model using the data collected from Bassani-Sternberg et al. as described in Example 1 as training data, filtered by the same method. The peptides and corresponding HLA types which are identified as presented peptide-HLA complexes were used as positive training data. The same peptide sequences paired with other HLA types were considered negative training data. The binding affinity of each peptide to their corresponding HLA type and the gene expression level for each peptide were obtained as described above. A logistic regression model was built with the peptide binding affinity to MHC class I complex and the gene expression level for peptides as features and using LogisticRegression in Scikit-learn to predict peptide presentation by MHC class I. A ten-fold cross-validation was performed and the accuracy and AUC of ROC for the testing dataset of the training data are listed in Table 1. In this model, the binding affinity contributes more strongly than gene expression.

Example 3. Prediction of Peptide Presentation by MHC Class I Complex by Considering the Peptide Binding Affinity and the Protein Abundance Besides the ability of peptides to bind to MHC class I complex, the abundance of peptides can also affect the amount of peptides that are presented by the MHC complex. In this example, peptide abundance is also considered. We built a model with selected features to predict peptide presentation by MHC class I complex by accounting for the peptide binding ability to MHC class I complex and the abundance of peptides.

We built a model to predict MHC class I presentation by considering two properties affecting the peptide binding ability and peptide binding probability to MHC class I complex, the binding affinity of peptides and the abundance of peptides, respectively. We calculated the binding affinity of a peptide to MHC class I complex as described in Example 1. The abundance of a peptide in this example is represented by the protein abundance for the peptide, which is defined as the maximum abundance of the proteins containing the peptide and produced from a gene. We obtained the protein abundance for peptides using the *H. sapiens*—Whole organism (Integrated) database of the PaxDb Protein Abundance Database (Wang, M. et al., Proteomics 2015, 10.1002/pmic.201400441). We trained a machine learning model using the data collected from Bassani-Sternberg et al. as described in Example 1 as training data, filtered in the same way. The peptides and corresponding HLA types which are identified as presented peptide-HLA complexes were used as positive training data. The same peptide sequences paired with other HLA types were considered negative training data. The binding affinity of each peptide to their corresponding HLA type and the protein abundance for each peptide were calculated as described above. A logistic regression model was built with the peptide binding affinity to MHC class I complex and the protein abundance for peptides as features and using LogisticRegression in Scikit-learn to predict peptide presentation by MHC class I. A ten-fold cross-validation was performed and the accuracy and AUC of ROC for the testing dataset of the training data are listed in Table 1. In this exercise, we found that binding affinity contributes more strongly to the model than protein abundance.

Example 4. Prediction of Peptide Presentation by MHC Class II Complex by Considering the Peptide Binding Affinity to MHC Class II Complex In order for a peptide to be an antigen, it needs to be able to be presented to the surface of a cell by the MHC complex to be recognized by immune cells. This process includes peptide presentation by MHC class II complex in antigen presentation cells to present the peptide to CD4+ T cells, peptide presentation by MHC class I complex in antigen presentation cells to present the peptide to CD8+ T cells and peptide presentation by MHC class I complex in tumor cells to CD8+ T cells. In this example, we built a model to predict peptide presentation by MHC class II complex.

We built a model to predict MHC class II presentation by considering the binding affinity of peptides to MHC class II complex. Peptide binding affinity to MHC class II complex was calculated using NetMHCII2.2 (Nielsen M, et al., BMC Bioinformatics. 2007 Jul. 4; 8:238). For the HLA types that were not available, NetMHCIIpan3.1 (Andreatta M, et al., Immunogenetics. 2015 November; 67(11-12): 641-50) was used to calculate the peptide binding affinity. We trained a machine learning model using the data collected from Chong et al., Molecular & Cellular Proteomics, 2017 as training data. The peptide sequences whose lengths are smaller than 9 are removed from the training data. The peptides and corresponding HLA types which are identified as presented peptide-HLA complexes were used as positive training data. The same peptide sequences paired with other HLA types were considered negative training data. A logistic regression model was built using the peptide binding affinity to MHC class II complex as the feature and using LogisticRegression in Scikit-learn to predict peptide presentation by MHC class II. A ten-fold cross-validation was performed and the accuracy and AUC of ROC for the testing dataset of the training data are listed in Table 1.

TABLE 1

Model performance of Example 1-4.

|  | Example 1 (MHC Class I) | Example 2 (MHC Class I) | Example 3 (MHC Class I) | Example 4 (MHC Class II) |
|---|---|---|---|---|
| AUC of ROC | 0.88 | 0.88 | 0.88 | 0.78 |
| Accuracy | 0.82 | 0.81 | 0.81 | 0.71 |

Example 5. Prediction of the Ability for Peptides to Stimulate Immune Response of CD4+ T Cells by Considering the Self-Similarity for MHC Class II and the Peptide Homology with Known Antigens In order for a peptide to be an antigen with immunogenicity, besides presentation by MHC class I and class II complex, the ability of the peptide to stimulate immune response of CD4+ and CD8+ T cells is also important. In this example, we built a model with selected features to predict the ability of peptides to stimulate CD4+ T cell immune response.

We built a model to predict the ability of peptides to stimulate CD4+ T cell immune response by considering two properties of a peptide affecting the recognition by CD4+ T cells. The properties are the similarity between the peptide and the human protein sequences for MHC class II (referred to as self-similarity for MHC Class II) and the peptide homology with known antigens. We calculated the self-similarity for MHC Class II of a peptide in three steps. First, we retrieved all protein sequences from ENSEMBL GRch37 (www.ensembl.org/), and trimmed to all possible lengths of 9-23 amino acids. Due to that not all peptide sequences are mutated peptides, we mimicked the relationship of mutated peptide to wildtype peptide on all peptides. In other words, we aligned each peptide to the trimmed human-protein sequences, and we selected those with equal lengths and with only one mismatch. These selected, trimmed human-protein sequences are considered as self-peptides. Second, we calculated the binding affinity of the peptide and its corresponding self-peptide to the MHC class II complex as described in Example 4. Third, we defined the self-similarity for MHC Class II as the smaller binding affinity divided by the larger one. For the peptides that have two or more mismatches to human sequences, we assigned 0 as their self-similarity. We calculated the peptide homology by aligning the peptide sequences with known antigens using BLAST (https://blast.ncbi.nlm.nih.gov/Blast.cgi). Known antigen sequences were retrieved from the antigen data set of the IEDB database (www.iedb.org), selecting those labeled with viral or bacterial antigens. The peptides with a higher proportion of sequences aligned with a known antigen is considered as homologous. For the peptides that did not match with any known antigen, their peptide homology is assigned 0. We trained a machine learning model for predicting immune response of CD4+ T cells using the data whose file name is "tcell_full_v3.csv" and MHC class is labeled as "II" with labeled CD4+ T cell immune response outcomes collected from the IEDB database (http:// www.iedb.org) as training data. The data whose peptide lengths are not between 9 and 30, whose cell type is not a normal T cell and whose assay group is not labeled as immune signal release, T cell activation and T cell-APC binding are removed from the training data. A logistic regression model was built with the self-similarity for MHC Class II and the peptide homology with known antigens as features and using LogisticRegression in Scikit-learn to predict the ability of peptides to stimulate CD4+ T cell immune response. A ten-fold cross-validation was performed on the model and the accuracy and AUC of ROC for the testing dataset of the training data are listed in Table 2.

Figure 3A:
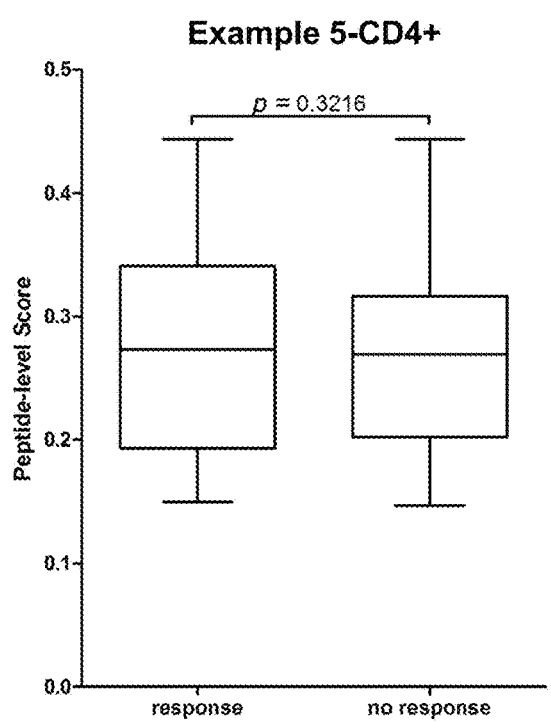
FIG. 3. Immune response comparison by T-cell features. Distribution of peptide-level score of peptides with immune response and no response. A) Example 5 considers self-similarity and antigen homology for CD4+ cells. B) Example 6 considers T-cell immunogenicity for CD8+ cells. P-values are calculated by Wilcoxon rank-sum test.

After model training, we tested the model using the data that were experimentally tested for T cell immune response with labeled CD4+ T cell immune response outcomes collected from Ott P et al., Nature, 2017 as testing data. We performed feature calculation as described above and calculated the prediction score for the model with the calculated features and trained parameters for each peptide in the testing data. The boxplot of the prediction score for the positive response and negative response data and the p-value calculated from Wilcoxon rank-sum test are showed in FIG. 3A.

Example 6. Prediction of the Ability for Peptides to Stimulate Immune Response of CD8+ T Cells by Considering the Peptide Immunogenicity In order for a peptide to be an antigen with immunogenicity, besides presentation by MHC class I and class II complex, the ability of the peptide to stimulate immune response of CD4+ and CD8+ T cells is also important. In this example, we built a model with selected feature to predict the ability of peptides to stimulate CD8+ T cell immune response.

Figure 3B:
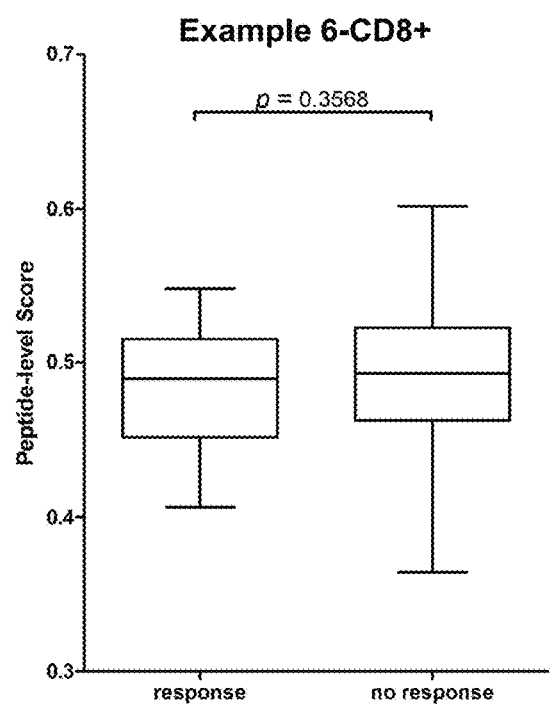

We built a model to predict the ability of peptides to stimulate CD8+ T cell immune response by considering a property of a peptide affecting the recognition by CD8+ T cells. The property is the immunogenicity of the peptide. We calculated the immunogenicity of a peptide using IEDB immunogenicity predictor (Calis J J, PLoS Comput Biol. (2013) Oct. 9(10): e1003266). We trained a machine learning model for predicting immune response of CD8+ T cells using the data whose file name is "tcell_full_v3.csv" and MHC class is labeled as "I" with labeled CD8+ T cell immune response outcomes collected from the IEDB database (http://www.iedb.org) as training data. The data whose peptide lengths are not between 8 and 11, whose cell type is not a normal T cell and whose assay group is not labeled as immune signal release, T cell activation and T cell-APC binding are removed from the training data. A logistic regression model was built with the peptide immunogenicity predicted by the IEDB immunogenicity predictor as the feature and using LogisticRegression in Scikit-learn to predict the ability of peptides to stimulate CD8+ T cell immune response. A ten-fold cross-validation was performed on the model and the accuracy and AUC of ROC for the testing dataset of the training data are listed in Table 2. After model training, we tested the model using the data that were experimentally tested for T cell immune response with labeled CD8+ T cell immune response outcomes collected from Ott P et al., Nature, 2017 as testing data. We performed feature calculation as described above and calculated the prediction score for the model with the calculated feature and trained parameters for each peptide in the testing data. The boxplot of the prediction score for the positive response and negative response data and the p-value calculated from Wilcoxon rank-sum test are showed in FIG. 3B.

Example 7. Prediction of the Ability for Peptides to Stimulate Immune Response of CD4+ T Cells by Considering the Self-Similarity for MHC Class II, the Peptide Homology with Known Antigens and the Feature in Example 4

The immune response of CD4+ T cells require the epitopes to be presented to the CD4+ T cells by antigen presenting cells. In this example, we built a model with selected features to predict the ability of peptides to stimulate CD4+ T cell immune response by accounting for both the ability of a peptide to stimulate immune response and also the ability for the peptide to be presented by MHC class II on antigen presenting cells.

We built a model to predict the ability of peptides to stimulate CD4+ T cell immune response by considering properties of a peptide affecting the recognition by CD4+ T cells and the presentation by MHC Class II complex. The properties are the self-similarity for MHC Class II, the peptide homology with known antigens and the binding affinity of the peptide to MHC class II complex. We calculated the self-similarity for MHC Class II and the homology with the known antigens as described in Example 5, and the binding affinity to MHC class II complex as described in Example 4. We trained a machine learning model for predicting immune response of CD4+ T cells using the data with labeled CD4+ T cell immune response outcomes collected from the IEDB database as training data as described in Example 5. The data filtering process is same as the one described in Example 5. A logistic regression model was built with the self-similarity for MHC Class II, the peptide homology with known antigens and the peptide binding affinity to MHC class II complex as features and using LogisticRegression in Scikit-learn to predict the ability of peptides to stimulate CD4+ T cell immune response. A ten-fold cross-validation was performed on the model and the accuracy and AUC of ROC for the testing dataset of the training data are listed in Table 2. In this example, we found that peptide binding affinity to MHC class II complex is a stronger predictor than self-similarity for MHC class II and peptide homology to known antigens.

Figure 4A:
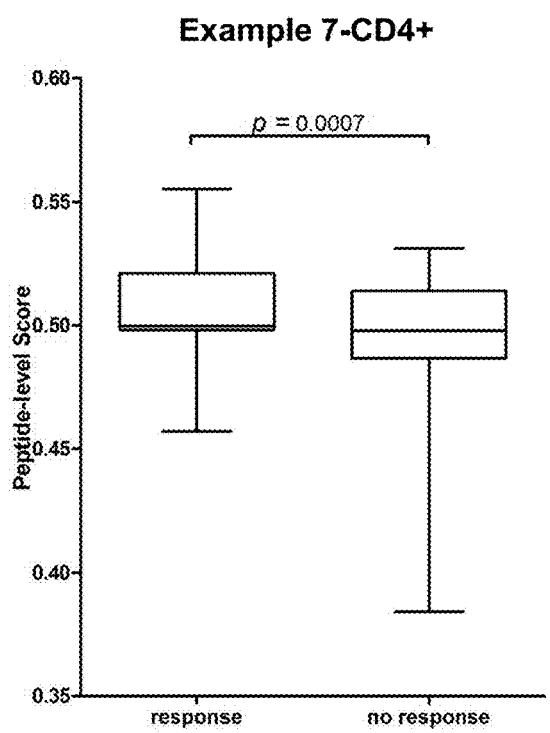
FIG. 4. Immune response comparison by antigen presentation features and T-cell features. Distribution of peptide-level score of peptides with immune response and no response. A) Example 7 considers self-similarity, antigen homology and features in Example 4 for CD4+. B) Example 8 considers T-cell immunogenicity and features in Example 1 for CD8+. P-values are calculated by Wilcoxon rank-sum test.

After model training, we tested the model using the data with labeled CD4+ T cell immune response outcomes collected from Ott P et al. as testing data as described in Example 5. We performed feature calculation as described above and calculated the prediction score for the model with the calculated features and trained parameters for each peptide in the testing data. The boxplot of the prediction score for the positive response and negative response data and the p-value calculated from Wilcoxon rank-sum test are showed in FIG. 4A.

Example 8. Prediction of the Ability for Peptides to Stimulate Immune Response of CD8+ T Cells by Considering the Peptide Immunogenicity and the Features in Example 1

The immune response of CD8+ T cells require the epitopes to be presented to the CD8+ T cells by MHC class I. In this example, we built a model with selected features to predict the ability of peptides to stimulate CD8+ T cell immune response by accounting for both the ability of a peptide to stimulate immune response and also the ability for the peptide to be presented by MHC class I.

We built a model to predict the ability of peptides to stimulate CD8+ T cell immune response by considering properties of a peptide affecting the recognition by CD8+ T cells and the presentation by MHC Class I complex. The properties are the immunogenicity of the peptide, the binding affinity and binding stability of the peptide to MHC class I complex. We calculated the peptide immunogenicity as described in Example 6, and the binding affinity and binding stability to MHC class I complex as described in Example 1. We trained a machine learning model for predicting immune response of CD8+ T cells using the data with labeled CD8+ T cell immune response outcomes collected from the IEDB database as training data as described in Example 6. The data filtering process is same as the one described in Example 6. A logistic regression model was built with the peptide immunogenicity, the peptide binding affinity and peptide binding stability to MHC class I complex as features and using LogisticRegression in Scikit-learn to predict the ability of peptides to stimulate CD8+ T cell immune response. A ten-fold cross-validation was performed on the model and the accuracy and AUC of ROC for the testing dataset of the training data are listed in Table 2. We found that peptide binding stability contributed the most in this model, followed by peptide binding affinity, and finally, peptide immunogenicity.

Figure 4B:
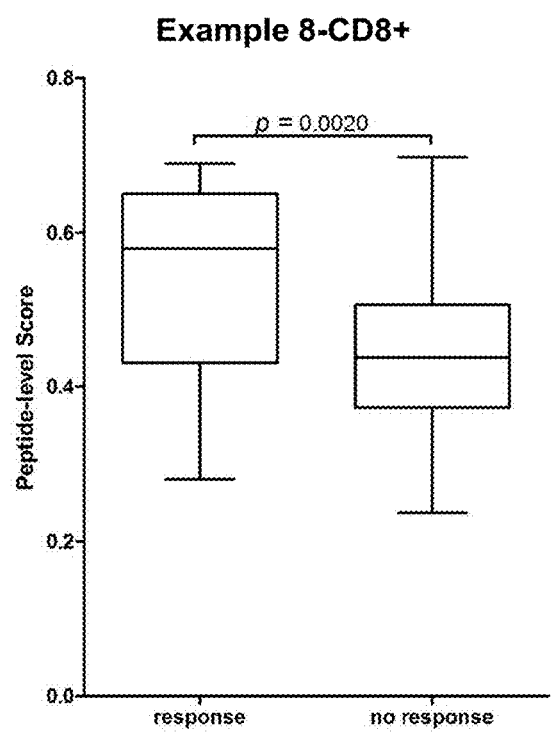

After model training, we tested the model using the data with labeled CD8+ T cell immune response outcomes collected from Ott P et al. as testing data as described in Example 6. We performed feature calculation as described above and calculated the prediction score for the model with the calculated features and trained parameters for each peptide in the testing data. The boxplot of the prediction score for the positive response and negative response data and the p-value calculated from Wilcoxon rank-sum test are showed in FIG. 4B.

Example 9. Prediction of the Ability for Peptides to Stimulate Immune Response of CD4+ T Cells by Considering the Self-Similarity for MHC Class II, the Peptide Homology with Known Antigens and the Prediction Score of the Model in Example 4

The immune response of CD4+ T cells require the epitopes to be presented to the CD4+ T cells by antigen presenting cells. In this example, we built a model with selected features to predict the ability of peptides to stimulate CD4+ T cell immune response by accounting for both the ability of a peptide to stimulate immune response and also the ability for the peptide to be presented by MHC class II on antigen presenting cells by considering that model built in Example 4.

We built a model to predict the ability of peptides to stimulate CD4+ T cell immune response by considering properties of a peptide affecting the recognition by CD4+ T cells and the presentation by MHC Class II complex. The properties are the self-similarity for MHC Class II, the peptide homology with known antigens and the prediction score of the MHC class II presentation model described in Example 4. We calculated the self-similarity for MHC Class II and the homology with the known antigens as described in Example 5. We calculated the binding affinity to MHC class II complex as described in Example 4 for calculating the prediction score of the MHC class II presentation model. We calculated the prediction score of the MHC class II presentation model with the calculated feature described above and trained parameters obtained from Example 4. We trained a machine learning model for predicting immune response of CD4+ T cells using the data with labeled CD4+ T cell immune response outcomes collected from the IEDB database as training data as described in Example 5. The data filtering process is same as the one described in Example 5. A logistic regression model was built with the self-similarity for MHC Class II, the peptide homology with known antigens and the prediction score of the MHC class II presentation model as features and using LogisticRegression in Scikit-learn to predict the ability of peptides to stimulate CD4+ T cell immune response. A ten-fold cross-validation was performed on the model and the accuracy and AUC of ROC for the testing dataset of the training data are listed in Table 2.

Figure 5A:
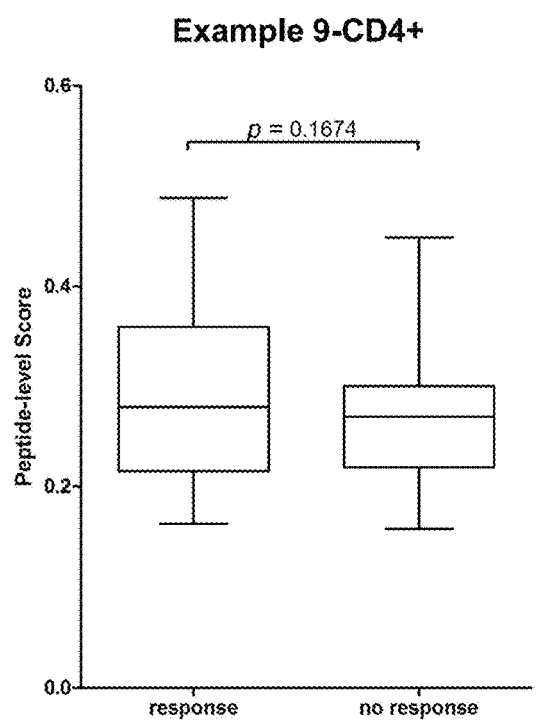
FIG. 5. Immune response comparison by antigen prediction score and T-cell features. Distribution of peptide-level score of peptides with immune response and no response. A) Example 9 considers self-similarity, antigen homology and prediction score of the model in Example 4 for CD4+. B) Example 10 considers T-cell immunogenicity and prediction score of the model in Example 1 for CD8+. P-values are calculated by Wilcoxon rank-sum test.

After model training, we tested the model using the data with labeled CD4+ T cell immune response outcomes collected from Ott P et al. as testing data as described in Example 5. We performed feature calculation as described above and calculated the prediction score for the model with the calculated features and trained parameters for each peptide in the testing data. The boxplot of the prediction score for the positive response and negative response data and the p-value calculated from Wilcoxon rank-sum test are showed in FIG. 5A.

Example 10. Prediction of the Ability for Peptides to Stimulate Immune Response of CD8+ T Cells by Considering the Peptide Immunogenicity and the Prediction Score of the Model in Example 1

The immune response of CD8+ T cells require the epitopes to be presented to the CD8+ T cells by MHC class I. In this example, we built a model with selected features to predict the ability of peptides to stimulate CD8+ T cell immune response by accounting for both the ability of a peptide to stimulate immune response and also the ability for the peptide to be presented by MHC class I as modeled in Example 1.

We built a model to predict the ability of peptides to stimulate CD8+ T cell immune response by considering properties of a peptide affecting the recognition by CD8+ T cells and the presentation by MHC Class I complex. The properties are the immunogenicity of the peptide and the prediction score of the MHC class I presentation model described in Example 1. We calculated the peptide immunogenicity as described in Example 6. We calculated the binding affinity and binding stability to MHC class I complex as described in Example 1 for calculating the prediction score of the MHC class I presentation model. We calculated the prediction score of the MHC class I presentation model with the calculated feature described above and trained parameters obtained from Example 1. We trained a machine learning model for predicting immune response of CD8+ T cells using the data with labeled CD8+ T cell immune response outcomes collected from the IEDB database as training data as described in Example 6. The data filtering process is same as the one described in Example 6. A logistic regression model was built with the peptide immunogenicity and the prediction score of the MHC class I presentation model as features and using LogisticRegression in Scikit-learn to predict the ability of peptides to stimulate CD8+ T cell immune response. A ten-fold cross-validation was performed on the model and the accuracy and AUC of ROC for the testing dataset of the training data are listed in Table 2. In this model, the prediction score of the MHC class I presentation model contributes more than the peptide immunogenicity feature.

Figure 5B:
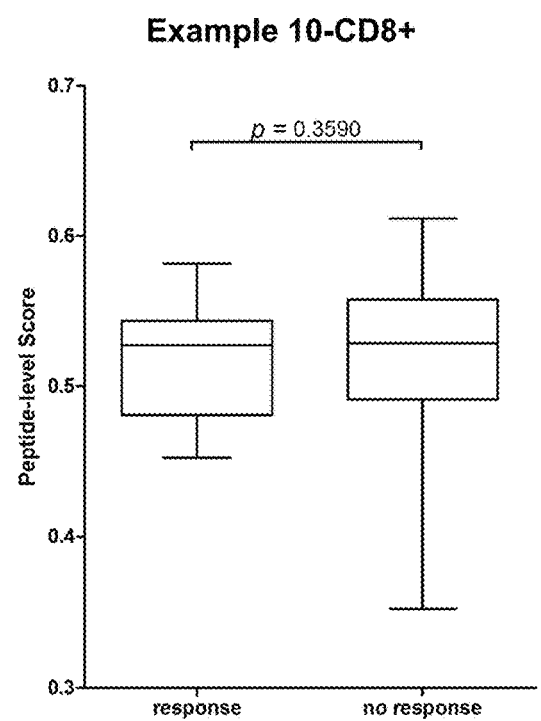

After model training, we tested the model using the data with labeled CD8+ T cell immune response outcomes collected from Ott P et al. as testing data as described in Example 6. We performed feature calculation as described above and calculated the prediction score for the model with the calculated features and trained parameters for each peptide in the testing data. The boxplot of the prediction score for the positive response and negative response data and the p-value calculated from Wilcoxon rank-sum test are showed in FIG. 5B.

TABLE 2

Model performance of Example 5-10.

|  | Example 5 (CD4+ T cells) | Example 6 (CD8+ T cells) | Example 7 (CD4+ T cells) | Example 8 (CD8+ T cells) | Example 9 (CD4+ T cells) | Example 10 (CD8+ T cells) |
|---|---|---|---|---|---|---|
| AUC of ROC | 0.59 | 0.56 | 0.58 | 0.64 | 0.59 | 0.61 |
| Accuracy | 0.59 | 0.55 | 0.6 | 0.62 | 0.63 | 0.59 |

Example 11. Prediction of the Peptides to be an Immunogen Considering Both Antigen Presentation and Immune Response from Example 1, 4-6

In order for a peptide to be able to elicit immune response, i.e. as an immunogen, the capabilities of the peptide to be presented by MHC class I and class II complex and also to stimulate CD4+ and CD8+ T cell response are required. Therefore, in this example, we integrated Example 1 and Examples 4 to 6 to predict the peptide as an immunogen by calculating the peptide-level score.

We built an integrated set of models by integrating antigen presentation information from Examples 1 and 4, and CD4+ and CD8+ information from Examples 5 and 6 to calculate the peptide-level score. The peptide-level score represents the capabilities of a peptide to be presented by MHC class I and class II complex and also to stimulate CD4+ and CD8+ T cell response. We calculated the peptide-level score by multiplying every prediction score calculated from Examples 1, 4, 5, and 6. To be noted, the peptides of MHC class II presentation and CD4+ T cell immune response prediction are longer than the peptides of MHC class I presentation and CD8+ T cell immune response. To resolve this, the features for MHC class II presentation and CD4+ T cell immune response were calculated from every possible longer peptide that contain the CD8+ peptide. The one with the strongest binding ability to stimulate CD4+ T cell immune response was selected for integrating the CD4+ and CD8+ information. We tested the peptide-level score using data labeled with CD8+ T cell immune response outcomes retrieved from Patrick A. Ott et al as testing data. We calculated the peptide-level score for each peptide in the testing data, and the boxplot of the prediction score for the positive response and negative response data and the p-value calculated by Wilcoxon rank-sum test are shown in FIG. 6A.

Example 12. Prediction of the Peptides to be an Immunogen Considering Both Antigen Presentation and Immune Response from Examples 7-8

As reasoned in Example 11, predicting peptide as an immunogen requires that the peptide to be presented by MHC class I and class II complex and also to stimulate CD4+ and CD8+ T cell response are required. In this example, we integrated Examples 7-8 to predict the peptide as an immunogen by calculating the peptide-level score.

We built an integrated set of models by integrating antigen presentation information and immune response information from Examples 7-8 to calculate the peptide-level score. The peptide-level score represents the capabilities of a peptide to be presented by MHC class I and class II complex and also to stimulate CD4+ and CD8+ T cell response. We calculated the peptide-level score by multiplying every prediction score calculated from Example 7-8. To be noted, the peptides of MHC class II presentation and CD4+ T cell immune response prediction are longer than the peptides of MHC class I presentation and CD8+ T cell immune response. To resolve this, the features for MHC class II presentation and CD4+ T cell immune response were calculated from every possible longer peptide that contain the CD8+ peptide. The one with the strongest binding ability to stimulate CD4+ T cell immune response was selected for integrating the CD4+ and CD8+ information. We tested the peptide-level score using data labeled with CD8+ T cell immune response outcomes retrieved from Patrick A. Ott et al as testing data. We calculated the peptide-level score for each peptide in the testing data, and the boxplot of the prediction score for the positive response and negative response data and the p-value calculated by Wilcoxon rank-sum test are shown in FIG. 6B.

Example 13. Prediction of the Peptides to be an Immunogen Considering Both Antigen Presentation and Immune Response from Examples 9-10

As reasoned in Example 11, predicting peptide as an immunogen requires that the peptide to be presented by MHC class I and class II complex and also to stimulate CD4+ and CD8+ T cell response are required. In this example, we integrated Examples 9-10 to predict the peptide as an immunogen by calculating the peptide-level score.

We built an integrated set of models by integrating antigen presentation information and immune response information from Examples 9-10 to calculate the peptide-level score. The peptide-level score represents the capabilities of a peptide to be presented by MHC class I and class II complex and also to stimulate CD4+ and CD8+ T cell response. We calculated the peptide-level score by multiplying every prediction score calculated from Example 9-10. To be noted, the peptides of MHC class II presentation and CD4+ T cell immune response prediction are longer than the peptides of MHC class I presentation and CD8+ T cell immune response. To resolve this, the features for MHC class II presentation and CD4+ T cell immune response were calculated from every possible longer peptide that contain the CD8+ peptide. The one with the strongest binding ability to stimulate CD4+ T cell immune response was selected for integrating the CD4+ and CD8+ information. We tested the peptide-level score using data labeled with CD8+ T cell immune response outcomes retrieved from Patrick A. Ott et al as testing data. We calculated the peptide-level score for each peptide in the testing data, and the boxplot of the prediction score for the positive response and negative response data and the p-value calculated by Wilcoxon rank-sum test are shown in FIG. 6C.

Figure 7:
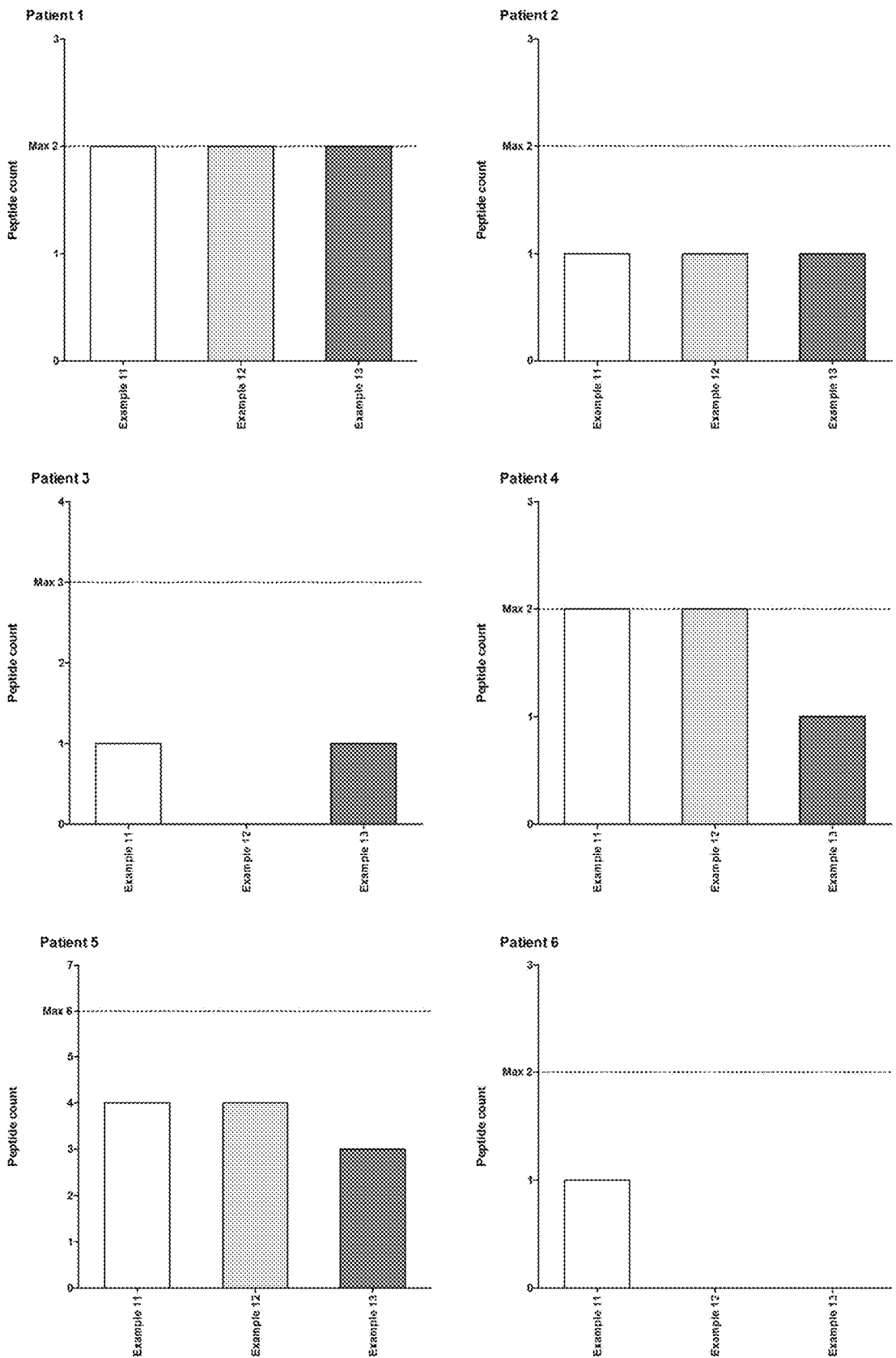
FIG. 7. Responding peptides in top 50 peptide-level scores. Bars show the number of peptides that were experimentally confirmed to respond to CD8+ and ranked in the top 50 peptide-level scores for each set. Each plot represents a specific patient. Dashed lines denote the total number of responding peptides in the patient.

Example 14. Identifying, Scoring, Ranking and Evaluating Peptides from Patient's Sample as Immunogens Using Peptide-Level Score To identify, score, rank, and evaluate peptides as immunogen for a patient, we retrieved and compared our scoring method on the peptides from Ott P et al. (Nature. 2017 Jul. 13; 547(7662):217-221). Ott P et al. synthesized immunizing long peptides (IMP) from six melanoma patients and experimentally tested the immunogenicity of the peptides on immune cells. These immunizing long peptides were of lengths ranging from 15 to 30 amino acids. The tested peptides were shorter, of lengths 9-10 amino acids for CD8+ response, and the responding peptides were identified. We hence retrieved the shorter, overlapping peptides from the immunizing long peptides, where the shorter peptides are of lengths 9-10 amino acids and harbor the mutated amino acid. We then calculated the peptide-level scores for the shorter peptides of each patient as described in Example 11-13. The peptides with the top 50 scores were selected, as 50 is a common number used in vaccine selection. Data for Patient 1 using Example 12 is shown in Table 3. We then show that the number of responding peptides that could elicit CD8+ response within the top 50 peptides for each patient calculated using Example 11-13 in FIG. 7.

TABLE 3

Top 50 Peptide-level score for Patient 1 using calculation from Example 12

| Rank | PatientID | IMPID | sequence | peptide-level score | CD8 response |
|---|---|---|---|---|---|
| 1 | 1 | 1-IMP04 | KLKFVTLVF | 0.345 | 1 |
| 2 | 1 | 1-IMP07 | RFLEYLPLRF | 0.336 | 1 |
| 3 | 1 | 1-IMP02 | VQKVASKIPF | 0.328 | 0 |
| 4 | 1 | 1-IMP06 | TLFHTFYEL | 0.321 | 0 |
| 5 | 1 | 1-IMP06 | TLFHTFYELL | 0.317 | 0 |
| 6 | 1 | 1-IMP11 | KFGDLTNNF | 0.303 | 0 |
| 7 | 1 | 1-IMP26 | PREEFLRLC | 0.302 | 0 |
| 8 | 1 | 1-IMP08 | KLFESKAEL | 0.299 | 0 |
| 9 | 1 | 1-IMP17 | LCPREEFLR | 0.298 | 0 |
| 10 | 1 | 1-IMP02 | PFPDRITEES | 0.297 | 0 |
| 11 | 1 | 1-IMP04 | VLAKKLKFV | 0.295 | 0 |
| 12 | 1 | 1-IMP03 | KKKWFLFQD | 0.292 | 0 |
| 13 | 1 | 1-IMP02 | PFPDRITEE | 0.291 | 0 |
| 14 | 1 | 1-IMP07 | HTELERFLE | 0.288 | 0 |
| 15 | 1 | 1-IMP08 | KLFESKAELA | 0.287 | 0 |
| 16 | 1 | 1-IMP07 | TELERFLEY | 0.286 | 0 |
| 17 | 1 | 1-IMP07 | LLHTELERF | 0.286 | 0 |
| 18 | 1 | 1-IMP02 | FPDRITEES | 0.285 | 0 |
| 19 | 1 | 1-IMP19 | VSVGDFSQEF | 0.283 | 0 |
| 20 | 1 | 1-IMP02 | IPFPDRITEE | 0.280 | 0 |
| 21 | 1 | 1-IMP17 | CPREEFLRLC | 0.280 | 0 |
| 22 | 1 | 1-IMP12 | ALFASRPRF | 0.279 | 0 |
| 23 | 1 | 1-IMP03 | FLFQDSKKI | 0.277 | 0 |
| 24 | 1 | 1-IMP08 | DKLFESKAE | 0.277 | 0 |
| 25 | 1 | 1-IMP03 | SKKKWFLFQD | 0.276 | 0 |
| 26 | 1 | 1-IMP02 | IPFPDRITE | 0.276 | 0 |
| 27 | 1 | 1-IMP12 | GGALFASRP | 0.276 | 0 |
| 28 | 1 | 1-IMP07 | LHTELERFLE | 0.275 | 0 |
| 29 | 1 | 1-IMP26 | LSPREEFLR | 0.275 | 0 |
| 30 | 1 | 1-IMP26 | SPREEFLRLC | 0.274 | 0 |
| 31 | 1 | 1-IMP19 | VGDFSQEFS | 0.272 | 0 |
| 32 | 1 | 1-IMP03 | KKKWFLFQDS | 0.271 | 0 |
| 33 | 1 | 1-IMP10 | DSGIPENSFN | 0.271 | 0 |
| 34 | 1 | 1-IMP19 | VGDFSQEFSP | 0.271 | 0 |
| 35 | 1 | 1-IMP12 | RGGALFASRP | 0.270 | 0 |
| 36 | 1 | 1-IMP19 | SVGDFSQEF | 0.269 | 0 |
| 37 | 1 | 1-IMP10 | LADSGIPEN | 0.267 | 0 |
| 38 | 1 | 1-IMP04 | KKLKFVTLV | 0.266 | 0 |
| 39 | 1 | 1-IMP02 | SKIPFPDRIT | 0.265 | 0 |
| 40 | 1 | 1-IMP10 | GIPENSFNV | 0.265 | 0 |
| 41 | 1 | 1-IMP02 | KIPFPDRIT | 0.264 | 0 |
| 42 | 1 | 1-IMP11 | GKFGDLTNN | 0.264 | 0 |
| 43 | 1 | 1-IMP08 | DSDKLFESK | 0.263 | 0 |
| 44 | 1 | 1-IMP08 | EDSDKLFES | 0.263 | 0 |
| 45 | 1 | 1-IMP07 | LLHTELERFL | 0.262 | 0 |
| 46 | 1 | 1-IMP12 | RRGGALFASR | 0.262 | 0 |
| 47 | 1 | 1-IMP10 | IPENSFNVS | 0.262 | 0 |
| 48 | 1 | 1-IMP02 | ASKIPFPDR | 0.261 | 0 |
| 49 | 1 | 1-IMP06 | LFHTFYELLI | 0.261 | 0 |
| 50 | 1 | 1-IMP07 | ILLHTELERF | 0.259 | 0 |

Example 15. Determining Sample-Level Score from Clonality of Mutated Alleles We calculated clonality of mutated allele from sample-specific data. We obtained formalin-fixed paraffin-embedded (FFPE) samples and paired peripheral blood mononuclear cell samples for each patient. Genomic DNA is extracted using QIAamp® DNA FFPE Tissue Kit (QIAGEN®, Hilden, Germany). DNA was amplified using multiplexed PCR targeting 18,136 pairs of amplicons. The exome of the sample was sequenced using Ion Proton™ (Thermo Fisher Scientific, Waltham, Mass.) system with the Ion PI Chip (Thermo Fisher Scientific, Waltham, Mass.) following manufacturer recommended protocol. Raw sequence reads were processed by the manufacturer provided software Torrent Variant Caller (TVC) v. 4.4, and .bam and .vcf files were generated. TVC also calculated variant frequency for each variant. The variants were annotated by Variant Effect Predictor v. 74. We then filtered out single nucleotide polymorphisms (SNPs) and germline mutations by dbSNP 138, 1000 Genome and the normal-paired blood. The remaining variants were checked manually. Copy number and tumor purity were determined from the .bam files by ONCOCNV and ADTEx respectively. Loss-of-heterozygosity (LOH) was determined by deviation >8% of SNP allele frequency of FFPE to normal-paired blood.

Clonality of mutated allele is based on assigning an expected number of mutated allele based on statistical significance of expected allele frequency and observed allele frequency, and then estimate subclonal purity. The expected allele frequency (McGranahan et al., Science (2016) Mar. 25; 351(6280):1463-9) is calculated as follows, $$AF_{expected} = \frac{pM}{pC_t + C_n(1-p)}$$

where $AF_{expected}$ denotes the expected allele frequency, t denotes the tumor variant, p denotes tumor purity, C denotes copy number, n denotes normal conditions, and M denotes mutated allele number. Assigning M is based on the closest observed allele frequency with $AF_{expected}$ with $\chi^2$ statistical significance, where $AF_{expected}$ is from the Table 4 (modified from Sun et al., Cancer Res (2014) 74(195):1893),

TABLE 4

Mutated allele number and expected Allele Frequency with respect to copy number, LOH, and tumor purity

| Copy Number* | LOH status | M | 0 | 0.10 | 0.20 | 0.30 | 0.40 | 0.50 | 0.60 | 0.70 | 0.80 | 0.90 | 1 |
|---|---|---|---|---|---|---|---|---|---|---|---|---|---|
| 1 | LOH | 1 | 0 | 0.05 | 0.11 | 0.18 | 0.25 | 0.33 | 0.43 | 0.54 | 0.67 | 0.82 | 1 |
| 2 | LOH | 2 | 0 | 0.10 | 0.20 | 0.30 | 0.40 | 0.50 | 0.60 | 0.70 | 0.80 | 0.90 | 1 |
| 2 | het | 1 | 0 | 0.05 | 0.10 | 0.15 | 0.20 | 0.25 | 0.30 | 0.35 | 0.40 | 0.45 | 0.50 |
| 3 | LOH | 3 | 0 | 0.14 | 0.27 | 0.39 | 0.50 | 0.60 | 0.69 | 0.78 | 0.86 | 0.93 | 1 |
| 3 | het | 1 | 0 | 0.05 | 0.09 | 0.13 | 0.17 | 0.20 | 0.23 | 0.26 | 0.29 | 0.31 | 0.33 |
| 3 | het | 2 | 0 | 0.10 | 0.18 | 0.26 | 0.33 | 0.40 | 0.46 | 0.52 | 0.57 | 0.62 | 0.67 |
| 4 | LOH | 4 | 0 | 0.18 | 0.33 | 0.46 | 0.57 | 0.67 | 0.75 | 0.82 | 0.89 | 0.95 | 1 |
| 4 | Het | 3 | 0 | 0.14 | 0.25 | 0.35 | 0.43 | 0.50 | 0.56 | 0.62 | 0.67 | 0.71 | 0.75 |
| 4 | Het | 1 | 0 | 0.05 | 0.08 | 0.12 | 0.14 | 0.17 | 0.19 | 0.21 | 0.22 | 0.24 | 0.25 |
| 4 | Het | 2 | 0 | 0.09 | 0.17 | 0.23 | 0.29 | 0.33 | 0.38 | 0.41 | 0.44 | 0.47 | 0.50 |
| ... | | | | | | | | | | | | | |

*only copy number ranging from 1-4 is shown, but calculation can be done on any copy number
**only tumor purity with an increment of 0.1 is shown, but calculation can be done on any tumor purity Using the assigned M, the subclonal purity s, can be calculated by $$s = \frac{AF_{observed}}{M}(pC_t + C_n(1-p))$$

The sample-level score was then determined by dividing subclonal purity s with tumor purity p, representing the actual dosage of mutated allele in the body.

$$\text{sample-level score} = \frac{s}{p}$$

Note that if the observed frequency is greater than expected frequency, we assumed the variant is a clonal mutation and did not perform the $\chi^2$ test. Moreover, under this situation, the subclonal purity is larger than tumor purity, and a sample-level score of 1 is assigned. The sample-level score for a sample is shown in Table 5.

TABLE 5

Sample-level score for a sample

| Variant | variant freq. | tumor purity | LOH | copy num | clonal | p-val | exp. freq. | sub-clonal purity | sample level score |
|---|---|---|---|---|---|---|---|---|---|
| ANK1 chr8_41552157_T > C | 0.723 | 66.8 | LOH | 2 | clonal | obs > exp | 0.668 | 0.723 | 1 |
| CHD5 chr1_6194848_G > A | 0.684 | 66.8 | LOH | 2 | clonal | obs > exp | 0.668 | 0.684 | 1 |

TABLE 5-continued

Sample-level score for a sample

| Variant | variant freq. | tumor purity | LOH | copy num | clonal | p-val | exp. freq. | sub-clonal purity | sample level score |
|---|---|---|---|---|---|---|---|---|---|
| SLC3A2 chr11_62652688_G > T | 0.408 | 66.8 | HET | 2 | clonal | obs > exp | 0.334 | 0.816 | 1 |
| MRC1 chr10_18122699_G > A | 0.407 | 66.8 | HET | 2 | clonal | obs > exp | 0.334 | 0.814 | 1 |
| TGS1 chr8_56698861_A > T | 0.392 | 66.8 | HET | 2 | clonal | obs > exp | 0.334 | 0.784 | 1 |
| SPACA1 chr6_88769199_C > A | 0.391 | 66.8 | HET | 2 | clonal | obs > exp | 0.334 | 0.782 | 1 |
| ARHGAP21 chr10_24896718_G > T | 0.38 | 66.8 | HET | 2 | clonal | obs > exp | 0.334 | 0.760 | 1 |
| NSRP1 chr17_28511815_G > T | 0.375 | 66.8 | HET | 2 | clonal | obs > exp | 0.334 | 0.750 | 1 |
| SCN3A chr2_165984466_C > T | 0.373 | 66.8 | HET | 2 | clonal | obs > exp | 0.334 | 0.746 | 1 |
| TET3 chr2_74328527_G > A | 0.373 | 66.8 | HET | 2 | clonal | obs > exp | 0.334 | 0.746 | 1 |
| ZDHHC1 chr16_67440152_C > T | 0.366 | 66.8 | HET | 2 | clonal | obs > exp | 0.334 | 0.732 | 1 |
| G0S2 chr1_209849154_T > G | 0.363 | 66.8 | HET | 2 | clonal | obs > exp | 0.334 | 0.726 | 1 |
| FANCM chr14_45645307_A > T | 0.354 | 66.8 | HET | 2 | clonal | obs > exp | 0.334 | 0.708 | 1 |
| NFASC chr1_204957844_G > A | 0.326 | 66.8 | HET | 2 | clonal | 0.637 | 0.334 | 0.652 | 0.977 |
| SON chr21_34921835_A > G | 0.636 | 66.8 | LOH | 2 | clonal | 0.585 | 0.668 | 0.636 | 0.953 |
| SSTR4 chr20_23017227_A > C | 0.636 | 66.8 | LOH | 2 | clonal | 0.209 | 0.668 | 0.636 | 0.953 |
| TMEM104 chr17_72832365_C > T | 0.317 | 66.8 | HET | 2 | clonal | 0.555 | 0.334 | 0.634 | 0.950 |
| ZC3H3 chr8_144557605_C > A | 0.315 | 66.8 | HET | 2 | clonal | 0.432 | 0.334 | 0.630 | 0.944 |
| KDELC2 chr11_108361810_T > C | 0.315 | 66.8 | HET | 2 | clonal | 0.765 | 0.334 | 0.630 | 0.944 |
| OSBPL5 chr11_3125480_G > A | 0.621 | 66.8 | LOH | 2 | clonal | 0.197 | 0.668 | 0.621 | 0.930 |
| TP53 chr17_7578445_A > T | 0.584 | 66.8 | LOH | 2 | subclonal | 0.028 | 0.668 | 0.584 | 0.875 |
| SP5 chr2_171572922_C > G | 0.291 | 66.8 | HET | 2 | clonal | 0.262 | 0.334 | 0.582 | 0.872 |
| COL6A5 chr3_130150786_C > A | 0.57 | 66.8 | LOH | 2 | subclonal | 0.006 | 0.668 | 0.570 | 0.854 |
| LRRC8E chr19_7964551_G > A | 0.564 | 66.8 | LOH | 2 | subclonal | 0.000 | 0.668 | 0.564 | 0.845 |
| NUP160 chr11_47809795_T > C | 0.274 | 66.8 | HET | 2 | clonal | 0.213 | 0.334 | 0.548 | 0.821 |
| ANO2 chr12_5685076_A > C | 0.41 | 66.8 | HET | 3 | subclonal | 0.010 | 0.5 | 0.547 | 0.819 |
| MUC16 chr19_9086656_C > T | 0.539 | 66.8 | LOH | 2 | subclonal | 0 | 0.668 | 0.539 | 0.807 |
| ARFGEF1 chr8_68208826_G > T | 0.265 | 66.8 | HET | 2 | clonal | 0.207 | 0.334 | 0.530 | 0.794 |
| APC2 chr19_1456374_GA > TT | 0.524 | 66.8 | LOH | 2 | subclonal | 0.000 | 0.668 | 0.524 | 0.785 |
| CSE1L chr20_47675019_A > T | 0.611 | 66.8 | LOH | 4 | subclonal | 0 | 0.801 | 0.509 | 0.763 |
| KCNA5 chr12_5154521_G > A | 0.382 | 66.8 | HET | 3 | subclonal | 0.003 | 0.5 | 0.510 | 0.763 |
| TRIM34 chr11_5664563_G > T | 0.454 | 66.8 | LOH | 2 | subclonal | 0 | 0.668 | 0.454 | 0.680 |
| CCDC141 chr2_179730534_C > T | 0.399 | 66.8 | LOH | 2 | subclonal | 0 | 0.668 | 0.399 | 0.598 |
| KIAA1429 chr8_95500959_C > A | 0.395 | 66.8 | LOH | 2 | subclonal | 0 | 0.668 | 0.395 | 0.592 |
| RNF17 chr13_25338358_C > T | 0.39 | 66.8 | LOH | 2 | subclonal | 0 | 0.668 | 0.390 | 0.584 |
| GBF1 chr10_104126933_A > G | 0.379 | 66.8 | LOH | 2 | subclonal | 0 | 0.668 | 0.379 | 0.568 |
| PRDX6 chr1_173454623_G > A | 0.367 | 66.8 | LOH | 2 | subclonal | 0 | 0.668 | 0.367 | 0.550 |

TABLE 5-continued

Sample-level score for a sample

| Variant | variant freq. | tumor purity | LOH | copy num | clonal | p-val | exp. freq. | sub-clonal purity | sample level score |
|---|---|---|---|---|---|---|---|---|---|
| GPR115 chr6_47681616_C > T | 0.359 | 66.8 | LOH | 2 | subclonal | 0 | 0.668 | 0.359 | 0.538 |
| DCHS1 chr11_6644247_C > A | 0.354 | 66.8 | LOH | 2 | subclonal | 0 | 0.668 | 0.354 | 0.530 |
| VPS13A chr9_79865083_A > T | 0.35 | 66.8 | LOH | 2 | subclonal | 0 | 0.668 | 0.350 | 0.524 |
| COL12A1 chr6_75851835_G > T | 0.345 | 66.8 | LOH | 2 | subclonal | 0 | 0.668 | 0.345 | 0.517 |
| EPN3 chr17_48616588_A > G | 0.341 | 66.8 | LOH | 2 | subclonal | 0 | 0.668 | 0.341 | 0.511 |
| SF3B1 chr2_198272747_T > C | 0.33 | 66.8 | LOH | 2 | subclonal | 0 | 0.668 | 0.330 | 0.494 |
| FAM65B chr6_24861205_C > A | 0.326 | 66.8 | LOH | 2 | subclonal | 0 | 0.668 | 0.326 | 0.488 |
| NF1 chr17_29509534_G > A | 0.323 | 66.8 | LOH | 2 | subclonal | 0 | 0.668 | 0.323 | 0.484 |
| C4BPA chr1_207317200_G > T | 0.317 | 66.8 | LOH | 2 | subclonal | 0 | 0.668 | 0.317 | 0.475 |
| DST chr6_56494089_T > A | 0.303 | 66.8 | LOH | 2 | subclonal | 0 | 0.668 | 0.303 | 0.454 |
| NALCN chr13_101944438_A > C | 0.284 | 66.8 | LOH | 2 | subclonal | 0 | 0.668 | 0.284 | 0.425 |
| NEK2 chr1_211836839_G > A | 0.261 | 66.8 | LOH | 2 | subclonal | 0 | 0.668 | 0.261 | 0.391 |
| HES1 chr3_193854752_C > G | 0.293 | 66.8 | LOH | 3 | subclonal | 0 | 0.751 | 0.261 | 0.390 |
| DOPEY1 chr6_83839042_C > T | 0.245 | 66.8 | LOH | 2 | subclonal | 0 | 0.668 | 0.245 | 0.367 |
| TATDN3 chr1_212981098_C > T | 0.111 | 66.8 | HET | 2 | subclonal | 0.001 | 0.334 | 0.222 | 0.333 |
| CCDC34 chr11_27360421_G > A | 0.148 | 66.8 | LOH | 2 | subclonal | 0 | 0.668 | 0.148 | 0.222 |
| SNX19 chr11_130785825_C > G | 0.145 | 66.8 | LOH | 2 | subclonal | 0 | 0.668 | 0.145 | 0.217 |
| CPS1 chr2_211441138_G > A | 0.12 | 66.8 | LOH | 2 | subclonal | 0 | 0.668 | 0.120 | 0.180 |
| PLOD1 chr1_12025537_G > A | 0.118 | 66.8 | LOH | 2 | subclonal | 0 | 0.668 | 0.118 | 0.177 |
| RBBP6 chr16_24579145_C > T | 0.117 | 66.8 | LOH | 2 | subclonal | 0 | 0.668 | 0.117 | 0.175 |
| DUT chr15_48634228_G > A | 0.114 | 66.8 | LOH | 2 | subclonal | 0 | 0.668 | 0.114 | 0.171 |
| LAMC1 chr1_183103819_G > A | 0.109 | 66.8 | LOH | 2 | subclonal | 0 | 0.668 | 0.109 | 0.163 |
| PELP1 chr17_4575375_C > T | 0.109 | 66.8 | LOH | 2 | subclonal | 0 | 0.668 | 0.109 | 0.163 |
| HAUS2 chr15_42858894_A > C | 0.103 | 66.8 | LOH | 2 | subclonal | 0 | 0.668 | 0.103 | 0.154 |
| RFC1 chr4_39322052_C > T | 0.103 | 66.8 | LOH | 2 | subclonal | 0 | 0.668 | 0.103 | 0.154 |
| TSSK2 chr22_19119814_C > T | 0.102 | 66.8 | LOH | 2 | subclonal | 0 | 0.668 | 0.102 | 0.153 |
| KBTBD12 chr3_127642629_G > A | 0.1 | 66.8 | LOH | 2 | subclonal | 0 | 0.668 | 0.100 | 0.150 |
| DCTN2 chr12_57939846_C > T | 0.109 | 66.8 | LOH | 3 | subclonal | 0 | 0.751 | 0.097 | 0.145 |

Example 16. Identifying, Scoring and Ranking Peptides from Cancer Sample as Immunogens Using Peptide-Level Score and Sample-Level Score To identify, score and rank peptides as immunogens for a cancer sample, we applied our scoring method on the peptides from the cancer samples. The exome sequencing process for the samples is described in Example 15. After the somatic mutations of the sample were confirmed, we retrieved the peptides harboring the mutated amino acids with the lengths between 8 to 23 amino acids. We then calculated the peptide-level scores as described in Example 12 and calculated the sample-level scores as described in Example 15 for the retrieved peptides. For integrating both the peptide and sample related information to rank each peptide as an immunogen, we calculated the immunogenic score for each peptide by multiplying the peptide-level score and the sample-level score of each peptide. The peptides from a gastric cancer sample with the top 50 immunogenic scores were selected and shown in Table 6.

TABLE 6

Top 50 immunogenic scores of a gastric cancer sample.

| Rank | VarID | sequence | Peptide-level score | Sample-level score | Immunogenic score |
|---|---|---|---|---|---|
| 1 | chr16_67440152_C > T | LYLFFAVIGFEILVPLLPHHW | 0.393 | 1.000 | 0.393 |
| 2 | chr16_67440152_C > T | LYLFFAVIGFEILVPLL | 0.390 | 1.000 | 0.390 |
| 3 | chr16_67440152_C > T | HPLQIVAWLLYLFFAVIGFEILV | 0.381 | 1.000 | 0.381 |
| 4 | chr17_28511815_G > T | RVNFRREKVIETPENDFKHHR | 0.379 | 1.000 | 0.379 |
| 5 | chr16_67440152_C > T | LYLFFAVIGFEI | 0.379 | 1.000 | 0.379 |
| 6 | chr10_18122699_G > A | STLTWHQAR | 0.369 | 1.000 | 0.369 |
| 7 | chr16_67440152_C > T | LYLFFAVIGFEIL | 0.364 | 1.000 | 0.364 |
| 8 | chr16_67440152_C > T | LYLFFAVIGFEILVPLLPHHWV | 0.363 | 1.000 | 0.363 |
| 9 | chr2_165984466_C > T | KMQECFQKAFFR | 0.359 | 1.000 | 0.359 |
| 10 | chr16_67440152_C > T | LYLFFAVIGFEILV | 0.358 | 1.000 | 0.358 |
| 11 | chr17_28511815_G > T | RVNFRREKVIETPENDFK | 0.352 | 1.000 | 0.352 |
| 12 | chr16_67440152_C > T | AWLLYLFFAVIGFEILVPLL | 0.350 | 1.000 | 0.350 |
| 13 | chr16_67440152_C > T | FFAVIGFEILVPLLPHHW | 0.350 | 1.000 | 0.350 |
| 14 | chr17_28511815_G > T | RVNFRREK | 0.349 | 1.000 | 0.349 |
| 15 | chr17_72832365_C > T | MYTLNFACCDVVGLAAVRFFL | 0.366 | 0.950 | 0.348 |
| 16 | chr10_18122699_G > A | TLTWHQAR | 0.345 | 1.000 | 0.345 |
| 17 | chr8_41552157_T > C | KLVPLVQAAFPENAVTKR | 0.344 | 1.000 | 0.344 |
| 18 | chr10_18122699_G > A | KSTLTWHQAR | 0.343 | 1.000 | 0.343 |
| 19 | chr16_67440152_C > T | AWLLYLFFAVIGFEI | 0.343 | 1.000 | 0.343 |
| 20 | chr8_41552157_T > C | KSKLVPLVQAAFPENAVTKR | 0.340 | 1.000 | 0.340 |
| 21 | chr1_209849154_T > G | ALFGVVLGRMETVCSPFTAAR | 0.338 | 1.000 | 0.338 |
| 22 | chr1_209849154_T > G | VVLGRMETVCSPFTAAR | 0.337 | 1.000 | 0.337 |
| 23 | chr1_209849154_T > G | KLYVLGSVLALFGVVLGR | 0.337 | 1.000 | 0.337 |
| 24 | chr10_18122699_G > A | STLTWHQARK | 0.336 | 1.000 | 0.336 |
| 25 | chr1_209849154_T > G | VVLGRMETVCSPFTAARRLR | 0.336 | 1.000 | 0.336 |
| 26 | chr10_24896718_G > T | KTSAPLIRR | 0.336 | 1.000 | 0.336 |
| 27 | chr17_72832365_C > T | MYTLNFACCDVVGLAAVRFF | 0.351 | 0.950 | 0.333 |
| 28 | chr8_41552157_T > C | VPLVQAAFPENAV | 0.333 | 1.000 | 0.333 |
| 29 | chr2_165984466_C > T | KMQECFQKAFFRK | 0.331 | 1.000 | 0.331 |
| 30 | chr17_72832365_C > T | MYTLNFACCDVVGLAAVRF | 0.348 | 0.950 | 0.331 |
| 31 | chr1_209849154_T > G | ALFGVVLGR | 0.330 | 1.000 | 0.330 |
| 32 | chr2_74328527_G > A | SLTEKPWALR | 0.329 | 1.000 | 0.329 |
| 33 | chr17_28511815_G > T | KSSADDEIEETRVNFR | 0.329 | 1.000 | 0.329 |
| 34 | chr8_56698861_A > T | KYLVEIVQESW | 0.329 | 1.000 | 0.329 |
| 35 | chr1_209849154_T > G | KMVKLYVLGSVLALFGVVLGR | 0.328 | 1.000 | 0.328 |
| 36 | chr1_209849154_T > G | ALFGVVLGRMETVCSPFTAARR | 0.328 | 1.000 | 0.328 |
| 37 | chr17_28511815_G > T | DEIEETRVNFRREKVIETPEND | 0.327 | 1.000 | 0.327 |

TABLE 6-continued

Top 50 immunogenic scores of a gastric cancer sample.

| Rank | VarID | sequence | Peptide-level score | Sample-level score | Immunogenic score |
|---|---|---|---|---|---|
| 38 | chr17_72832365_C > T | MYTLNFACCDVVGLAAVRFFLGL | 0.344 | 0.950 | 0.327 |
| 39 | chr2_74328527_G > A | STSALAGPSLTEKPWALR | 0.326 | 1.000 | 0.326 |
| 40 | chr6_88769199_C > A | KYMWKLLRQDQQSIILVNDSEI | 0.326 | 1.000 | 0.326 |
| 41 | chr17_28511815_G > T | DDEIEETRVNFRREKVIETPEND | 0.326 | 1.000 | 0.326 |
| 42 | chr1_209849154_T > G | RMETVCSPFTAAR | 0.326 | 1.000 | 0.326 |
| 43 | chr2_165984466_C > T | KMQECFQKAFFRKPK | 0.324 | 1.000 | 0.324 |
| 44 | chr10_24896718_G > T | KTSAPLIR | 0.324 | 1.000 | 0.324 |
| 45 | chr1_209849154_T > G | MVKLYVLGSVLALFGVVLGR | 0.323 | 1.000 | 0.323 |
| 46 | chr1_209849154_T > G | VLALFGVVLGRMETVCSPFTAAR | 0.323 | 1.000 | 0.323 |
| 47 | chr17_28511815_G > T | VNFRREKVIETPEND | 0.322 | 1.000 | 0.322 |
| 48 | chr17_28511815_G > T | ADDEIEETRVNFRREKVIETPEN | 0.320 | 1.000 | 0.320 |
| 49 | chr2_74328527_G > A | ALAGPSLTEKPWALR | 0.320 | 1.000 | 0.320 |
| 50 | chr1_209849154_T > G | SVLALFGVVLGR | 0.320 | 1.000 | 0.320 |

The invention claimed is:

1. A method for selecting at least one immunogenic mutated peptide, comprising:
   (a) obtaining a plurality of mutant sequences;
   (b) identifying at least one epitope that derived from a disease-associated mutation;
   (c) incorporating a plurality of factors associated with the immunogenicity of the at least one epitope, wherein the plurality of factors comprises a first factor that can be used to calculate a peptide-level score and a second factor that can be used to calculate a sample-level score, wherein the second factor for calculating said sample-level score comprises the clonality of the disease-associated mutation;

(d) weighing the plurality of factors;

(e) assigning an immunogenic score to the at least one epitope based on the weights of the plurality of factors;

(f) ranking the at least one epitope; and (g) selecting at least one immunogenic mutated peptide based on a ranking result in step (f), wherein the immunogenic mutated peptide comprises the at least one epitope that may elicit T-cell response.

2. The method of claim 1, wherein 100 or less epitopes are selected.

3. The method of claim 1, wherein 50 or less epitopes are selected.

4. The method of claim 1, wherein 30 or less epitopes are selected.

5. The method of claim 1, wherein 10 or less epitopes are selected.

6. The method of claim 1, wherein the plurality of factors accounts for the presentation of the at least one epitopes by MHC class I and class II.

7. The method of claim 5, wherein the binding affinity of the selected at least one epitope with MHC class I has an IC50 values less than 1500 nM.

8. The method of claim 5, wherein the plurality of factors comprises MHC class I binding stability.

9. The method of claim 5, wherein the plurality of factors comprises protein abundance, gene expression or a combination thereof.

10. The method of claim 1, wherein the plurality of factors accounts for the ability for the at least one epitopes to elicit immune response in cytotoxic T cells.

11. The method of claim 8, wherein the plurality of factors accounts for the ability for the at least one epitopes to elicit immune response in helper T cell.

12. The method of claim 9, wherein the plurality of factors comprises the similarity of the at least one epitope to self-peptide.

13. The method of claim 9, wherein the plurality of factors comprises the homology of the at least one epitope to a known antigens.

14. The method of claim 1, wherein the variant frequency of the mutation is at least 10%.

15. The method of claim 1, wherein the variant frequency of the mutation is at least 30%.

16. The method of claim 1, wherein the plurality of factors comprises copy number, tumor purity, or both copy number and tumor purity.

17. The method of claim 1, wherein one of the plurality of factors is the status of loss of heterozygosity.

18. The method of claim 1, wherein one of the plurality of factors is allele dosage.

19. The method of claim 1, wherein the immunogenic score is integrated from a plurality of factors including MHC class I and class II presentation of the at least one epitopes, the ability for the at least one epitopes to elicit immune response in both helper and cytotoxic T cells, and the clonality of the disease-associated mutation.

20. A system for selecting at least one immunogenic mutated peptide, comprising:

a hardware memory storing computer-executable means of:

(a) obtaining a plurality of mutant sequences;

(b) identifying at least one epitope that derived from a disease-associated mutation;

(c) incorporating a plurality of factors associated with the immunogenicity of the at least one epitope, wherein the plurality of factors comprises a first factor that can be used to calculate a peptide-level score and a second factor that can be used to calculate a sample-level score, wherein the second factor for calculating said sample-level score comprises the clonality of the disease-associated mutation;

(d) weighing the plurality of factors;

(e) assigning an immunogenic score to the at least one epitope based on the weights of the plurality of factors;

(f) ranking the at least one epitope; and (g) selecting at least one immunogenic mutated peptide based on a ranking result in the step (f), wherein the immunogenic mutated peptide comprises the at least one epitope that may elicit T-cell response.

* * * * *

UNITED STATES PATENT AND TRADEMARK OFFICE
CERTIFICATE OF CORRECTION

| | | |
|---|---|---|
| PATENT NO. | : 11,485,784 B2 | Page 1 of 1 |
| APPLICATION NO. | : 16/497442 | |
| DATED | : November 1, 2022 | |
| INVENTOR(S) | : Pei-Jia Yang | |

It is certified that error appears in the above-identified patent and that said Letters Patent is hereby corrected as shown below:

On the Title Page

Item (73) Assignee, Please change "ACT Genomics (IP) Co., Ltd." to --ACT Genomics (IP) Limited--.

Signed and Sealed this
Twenty-eighth Day of January, 2025

Coke Morgan Stewart
*Acting Director of the United States Patent and Trademark Office*